United States Patent
Ha et al.

(10) Patent No.: US 11,465,135 B2
(45) Date of Patent: Oct. 11, 2022

(54) BIFUNCTIONAL CHIRAL ORGANOCATALYTIC COMPOUND HAVING EXCELLENT ENANTIOSELECTIVITY, PREPARATION METHOD THEREFOR, AND METHOD FOR PRODUCING NON-NATURAL GAMMA-AMINO ACID FROM NITRO COMPOUND BY USING SAME

(71) Applicant: KOREA UNIVERSITY RESEARCH AND BUSINESS FOUNDATION, Seoul (KR)

(72) Inventors: Deok-Chan Ha, Seoul (KR); Jae Ho Shim, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 16/976,151

(22) PCT Filed: Jan. 24, 2019

(86) PCT No.: PCT/KR2019/001003
§ 371 (c)(1),
(2) Date: Aug. 27, 2020

(87) PCT Pub. No.: WO2019/168269
PCT Pub. Date: Sep. 6, 2019

(65) Prior Publication Data
US 2020/0406243 A1     Dec. 31, 2020

(30) Foreign Application Priority Data

Feb. 28, 2018 (KR) .................. 10-2018-0024695
Dec. 14, 2018 (KR) .................. 10-2018-0161967

(51) Int. Cl.
B01J 31/02      (2006.01)
C07C 335/12     (2006.01)
(Continued)

(52) U.S. Cl.
CPC ....... *B01J 31/0237* (2013.01); *B01J 31/0215* (2013.01); *B01J 31/0245* (2013.01);
(Continued)

(58) Field of Classification Search
None
See application file for complete search history.

(56) References Cited

FOREIGN PATENT DOCUMENTS

JP     2007-332129 A     12/2007

OTHER PUBLICATIONS

Han ("Discovery of Bifunctional Thiourea/Secondary-Amine Organocatalysts for the Highly Stereoselective Nitro-Mannich Reaction of alpha-Substituted Nitroacetates" Chem. Eur. J. 2008, 14, Supporting Information, p. S1-S66) (Year: 2008).*

(Continued)

*Primary Examiner* — Amy C Bonaparte
(74) *Attorney, Agent, or Firm* — NSIP Law

(57) ABSTRACT

The present invention relates to a bifunctional chiral organocatalytic compound having excellent enantioselectivity, a preparation method therefor, and a method for producing a non-natural gamma amino acid from a nitro compound by using the chiral organocatalytic compound. According to the present invention, the bifunctional chiral organocatalytic compound having excellent enantioselectivity can be easily synthesized, gamma-amino acids with high optical selectivity can be obtained at a high yield by an economical and convenient method using the chiral organocatalytic compound, and various (R)-configuration gamma-amino acids, which are not present in nature, can be produced with high optical purity in large quantities by using a small amount of a catalyst, and therefore, the present invention can be widely utilized in various industrial fields including the pharmaceutical industry.

1 Claim, 7 Drawing Sheets

1a $R_1$ = H, $R_2$ = Ph
1b $R_1$ = H, $R_2$ = 3,5-$(CF_3)_2$ Ph
1c $R_1$ = 3_pentyl, $R_2$ = p_tolyl
1d $R_1$ = 3_pentyl, $R_2$ = 3,5-$(CF_3)_2$ Ph
1e $R_1$ = 3_pentyl, $R_2$ = 4_$CF_3$_Ph
1f $R_1$ = 3_pentyl, $R_2$ = $C_6F_5$
1g $R_1$ = 3_pentyl, $R_2$ = 4_$NO_2$_Ph
1h $R_1$ = 3_pentyl, $R_2$ = 4_NC_Ph
1i $R_1$ = 3_pentyl, $R_2$ = 4_F_Ph
1j $R_1$ = $Ph_2$CH, $R_2$ = 3,5-$(CF_3)_2$ Ph
1k $R_1$ = $Ph_2$CH, $R_2$ = t_butyl
1l $R_1$ = $Ph_2$CH, $R_2$ = 4_$CF_3$_Ph
1m $R_1$ = 3,5-$(CF_3)_2$ $PhCH_2$, $R_2$ = 3,5-$(CF_3)_2$ Ph
1n $R_1$ = 3,5-$(CF_3)_2$ $PhCH_2$, $R_2$ = 3,5-$(Me)_2$ Ph

(51) Int. Cl.
  *C07C 335/16* (2006.01)
  *C07C 201/12* (2006.01)
  *C07C 227/22* (2006.01)
  *C07D 207/28* (2006.01)
  *C07C 205/04* (2006.01)
  *C07C 229/36* (2006.01)

(52) U.S. Cl.
  CPC .......... *C07C 201/12* (2013.01); *C07C 227/22* (2013.01); *C07C 335/12* (2013.01); *C07C 335/16* (2013.01); *C07D 207/28* (2013.01); *C07C 205/04* (2013.01); *C07C 229/36* (2013.01)

(56) References Cited

OTHER PUBLICATIONS

CAS(R) registry file for compound having registry No. RN 401-95-6, first entered into STN on Nov. 16, 1984 (Year: 1984).*

Han, Bo et al., "Discovery of Bifunctional Thiourea/Secondary-Amine Organocatalysts for the Highly Stereoselective Nitro-Mannich Reaction of α-Substituted Nitroacetates", *Chemistry—A European Journal*, vol. 14, Issue 27, Sep. 15, 2008 (4 pages in English).

Lu, Aidang et al., "Enantioselective Synthesis of trans-Dihydrobenzofurans via Primary Amine-Thiourea Organocatalyzed Intramolecular Michael Addition", *The Journal of Organic Chemistry*, vol. 77, Issue 14, Jun. 2012 (pp. 1-7).

Meninno, Sara et al., "Stereoselective amine-thiourea-catalysed sulfa-Michael/ nitroaldol cascade approach to 3,4,5-substituted tetrahydrothiophenes bearing a quaternary stereocenter", *Journal of Organic Chemistry*, Apr. 5, 2016 (pp. 643-647).

Nam, Si Hun., "Organocatalytic asymmetric Michael additions of Ketones to α, β-unsaturated nitro Compounds", Master's Thesis Paper, Korea University Graduate School, Department of Chemistry, Feb. 2017 (pp. 1-117).

Zhang, Jing et al., "Michael-Michael Addition Reactions Promoted by Secondary Amine-Thiourea: Stereocontrolled Construction of Barbiturate-Fused Tetrahydropyrano Scaffolds and Pyranocoumarins", The Journal of Organic Chemistry, Nov. 15, 2017 (pp. 1-9).

International Search Report dated May 15, 2019 in counterpart International Patent Application No. PCT/KR2019/001003 (3 pages in English and 3 pages in Korean).

* cited by examiner

[Fig. 1]
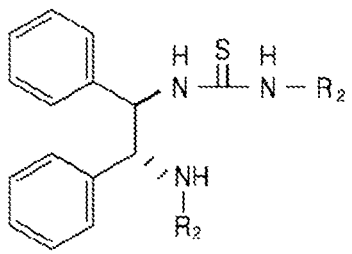
1a $R_1$ = H, $R_2$ = Ph
1b $R_1$ = H, $R_2$ = 3,5_$(CF_3)_2$ Ph
1c $R_1$ = 3_pentyl, $R_2$ = p_tolyl
1d $R_1$ = 3_pentyl, $R_2$ = 3,5_$(CF_3)_2$ Ph
1e $R_1$ = 3_pentyl, $R_2$ = 4_$CF_3$_Ph
1f $R_1$ = 3_pentyl, $R_2$ = $C_6F_5$
1g $R_1$ = 3_pentyl, $R_2$ = 4_$NO_2$_Ph
1h $R_1$ = 3_pentyl, $R_2$ = 4_NC_Ph
1i $R_1$ = 3_pentyl, $R_2$ = 4_F_Ph
1j $R_1$ = $Ph_2$CH, $R_2$ = 3,5_$(CF_3)_2$ Ph
1k $R_1$ = $Ph_2$CH, $R_2$ = t_butyl
1l $R_1$ = $Ph_2$CH, $R_2$ = 4_$CF_3$_Ph
1m $R_1$ = 3,5_$(CF_3)_2$ $PhCH_2$, $R_2$ = 3,5_$(CF_3)_2$ Ph
1n $R_1$ = 3,5_$(CF_3)_2$ $PhCH_2$, $R_2$ = 3,5_$(Me)_2$ Ph

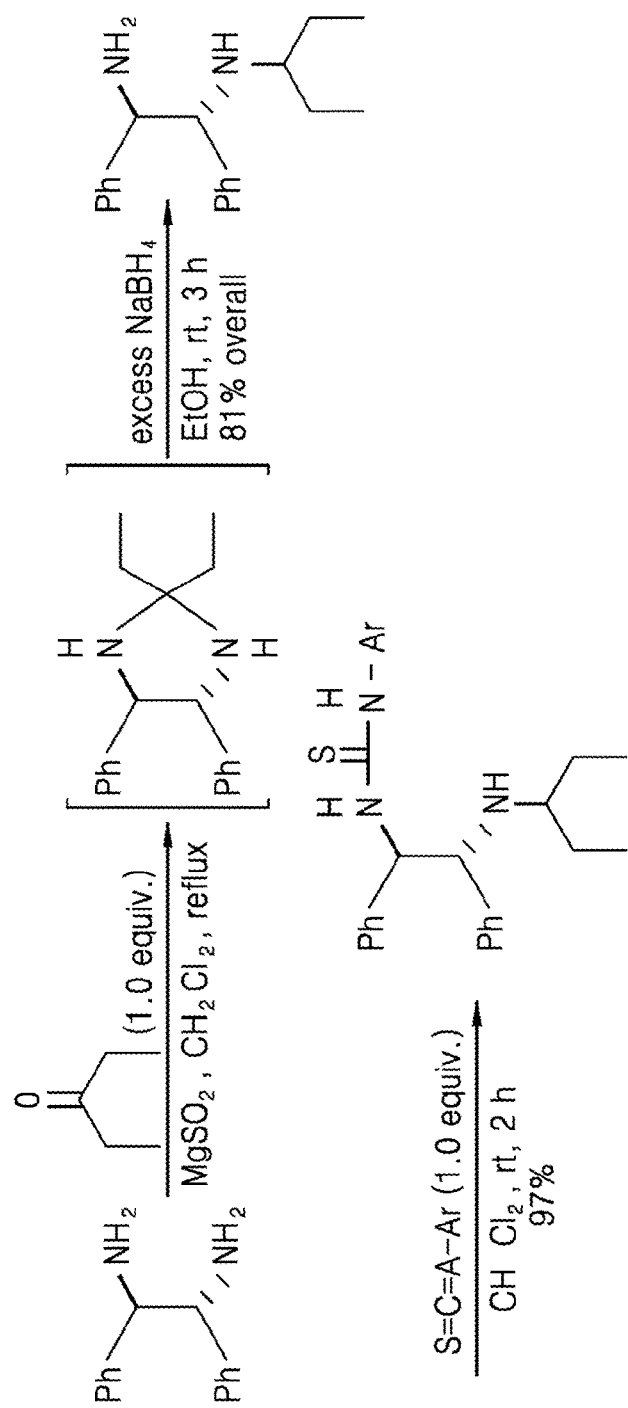
[Fig. 2]

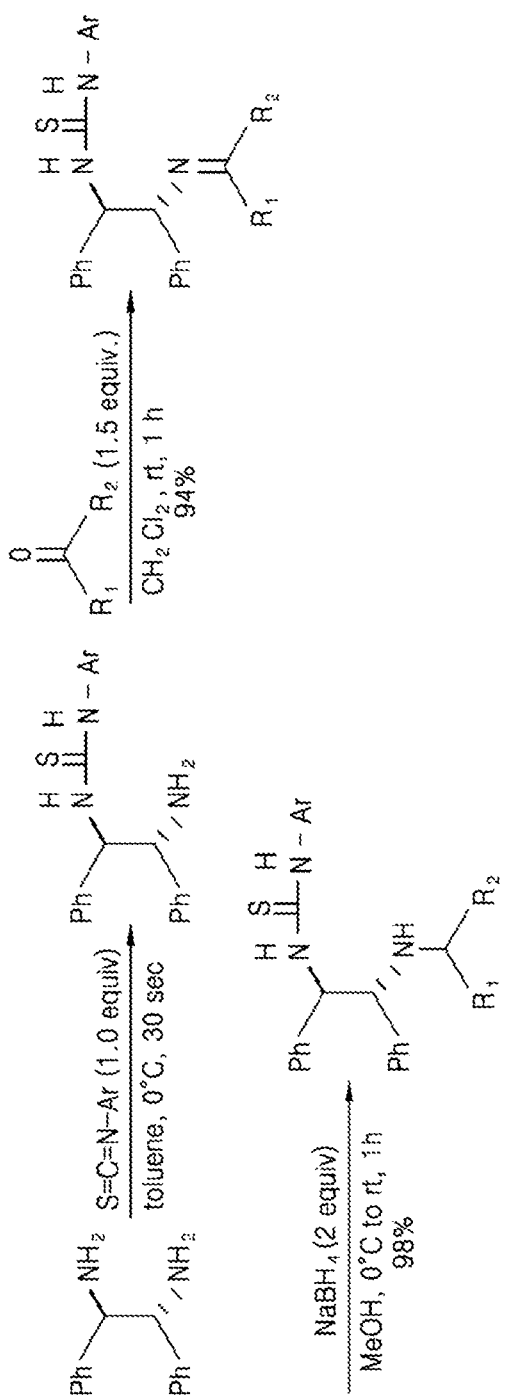
[Fig. 3]

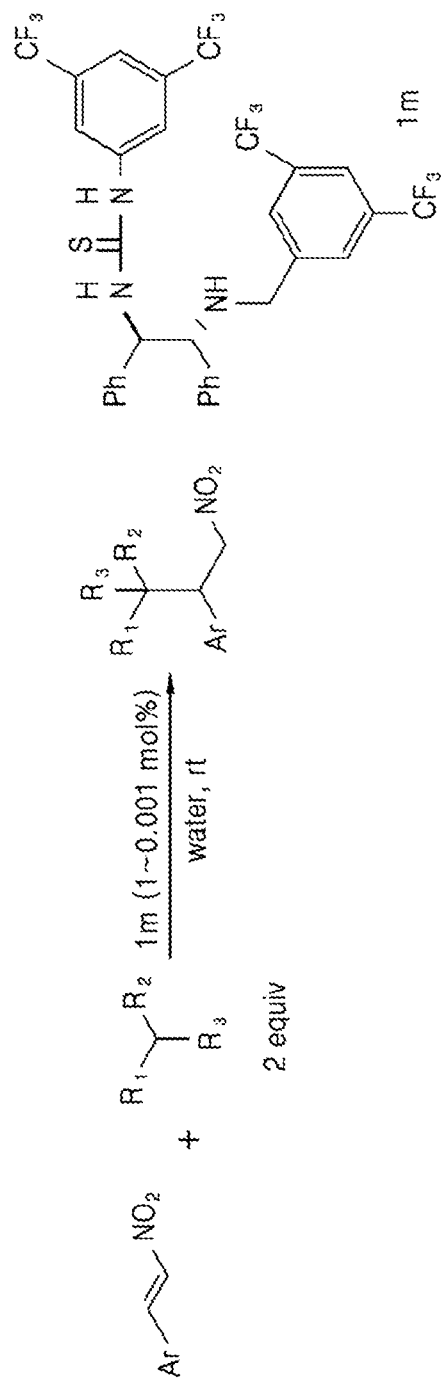
[Fig. 4]

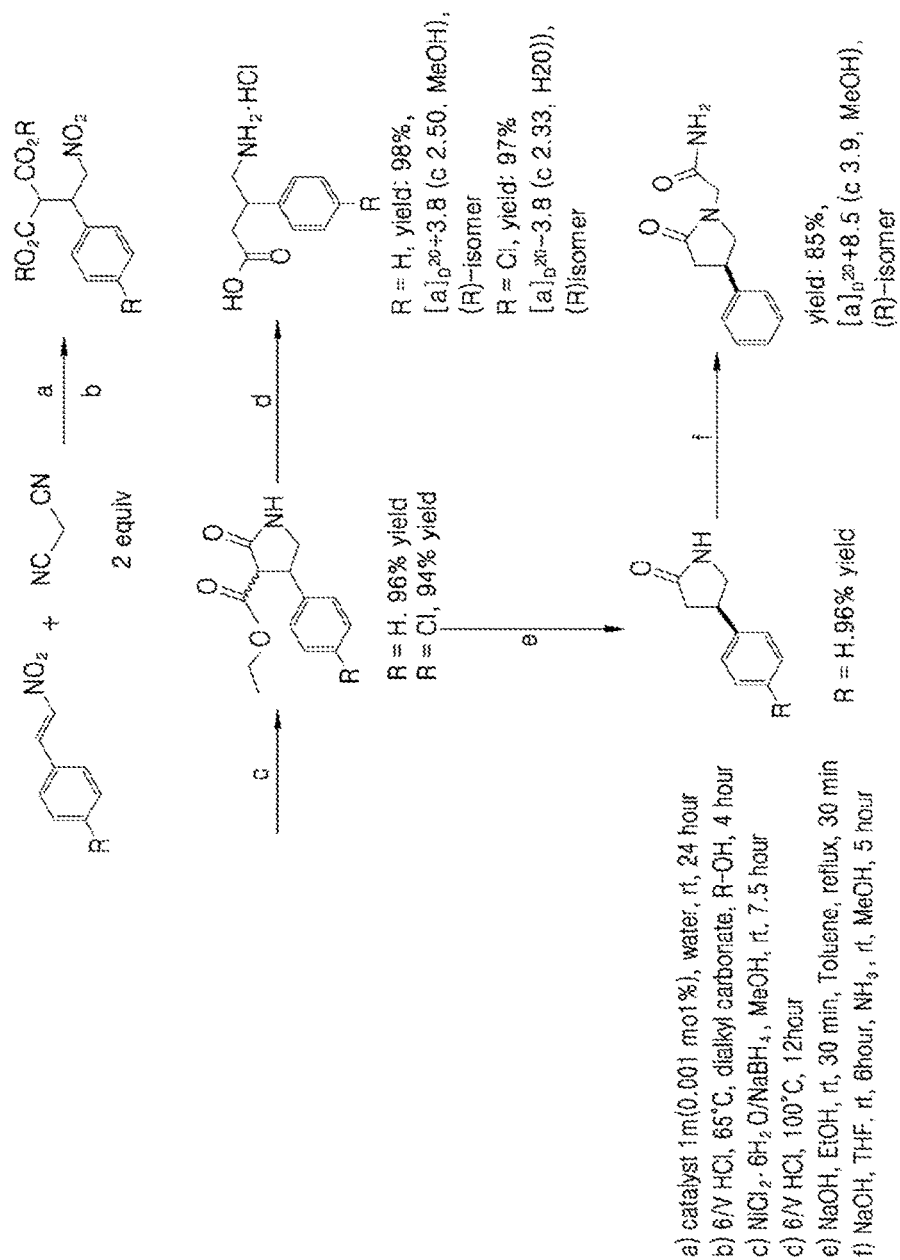
[Fig. 5]

[Fig. 6]
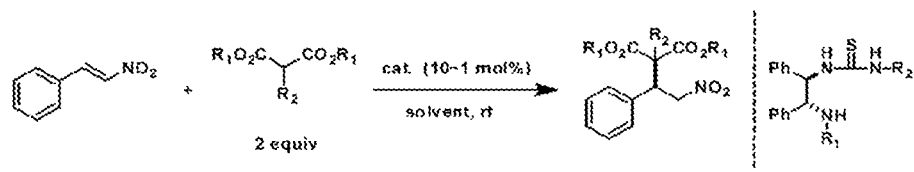
[Fig. 7]
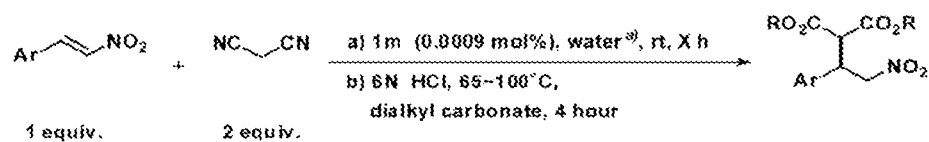
[Fig. 8]
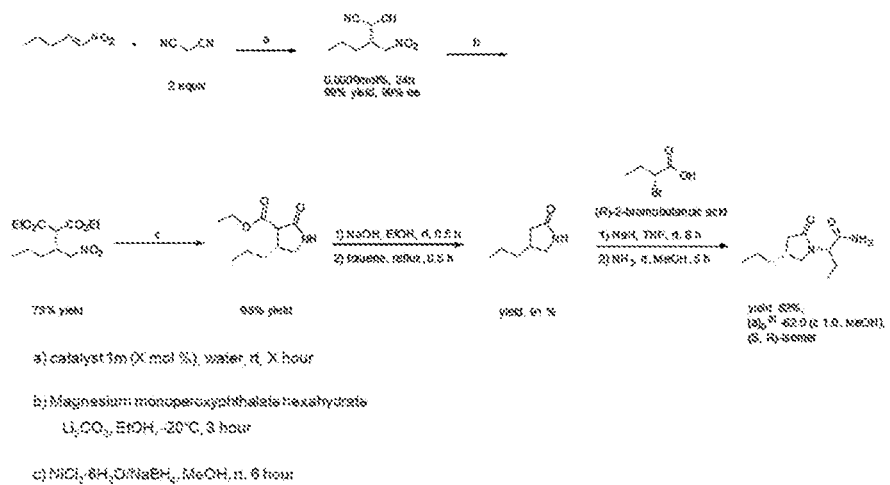

[Fig. 9]
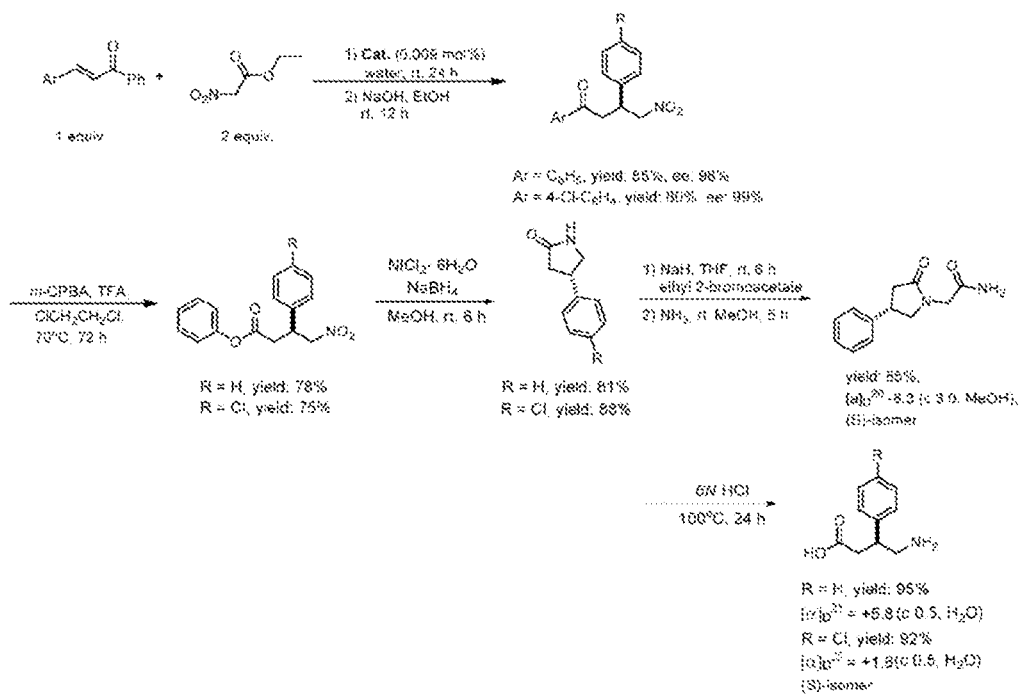

BIFUNCTIONAL CHIRAL ORGANOCATALYTIC COMPOUND HAVING EXCELLENT ENANTIOSELECTIVITY, PREPARATION METHOD THEREFOR, AND METHOD FOR PRODUCING NON-NATURAL GAMMA-AMINO ACID FROM NITRO COMPOUND BY USING SAME

CROSS REFERENCE TO RELATED APPLICATION(S)

This application is a U.S. National Stage Application of International Application No. PCT/KR2019/001003, filed on Jan. 24, 2019 and published as WO 2019/168269 on Sep. 6, 2019. This application and PCT/KR2019/001003 claim the benefit under 35 USC 119(a) and 365(b) of Korean Patent Application Nos. 10-2018-0024695 filed on Feb. 28, 2018 and 10-2018-0161967 filed on Dec. 14, 2018 in the Korean Intellectual Property Office. The disclosures of PCT/KR2019/001003 and Korean Patent Application Nos. 10-2018-0024695 and 10-2018-0161967 are incorporated herein by reference.

TECHNICAL FIELD

The present invention relates to a highly enantioselective chiral bifunctional organocatalyst, a method for preparing the chiral organocatalyst, and a method for producing an unnatural γ-amino acid from a nitro compound using the chiral organocatalyst.

BACKGROUND ART

Amino acids are basic structural units for proteins and are divided into natural amino acids and unnatural amino acids. Naturally occurring amino acids are used as sweeteners and animal feed, whereas unnatural amino acids corresponding to the isomers of natural amino acids are mainly used as raw materials for medicines.

Optically pure amino acids are employed as ligands of asymmetric catalysts or are widely used as starting materials or intermediates necessary for synthesizing a variety of pharmaceuticals and bioactive compounds. Accordingly, optically pure amino acids are considered industrially very important.

Fermentation is known as a useful method for producing amino acids in an inexpensive and economical manner but is limited to the production of natural L-amino acids. Optically pure D-amino acids and unnatural amino acids are currently produced by enzymatic resolution, optical resolution, and chiral resolution. However, the prices of amino acids produced by the current resolution methods are 5-10 times higher than those of natural L-amino acids produced by fermentation because the resolution methods involve high production costs. Further, the resolution methods have difficulty in producing amino acids on a large scale.

Some methods have been reported for recognizing the chiralities of chiral aminoalcohols and amino acids through imine bonds using binaphthol derivatives having an aldehyde group and converting L-amino acids to the corresponding D forms, but there is still a need to develop a method for producing an unnatural amino acid with high enantioselectivity in an economical and simple manner.

Under these circumstances, the present inventors have earnestly and intensively conducted research to solve the problems of the prior art, and as a result, found that even a small amount of a chiral organocatalyst having a specific structure is sufficient for the production of various types of unnatural γ-amino acids in high optical purity. The present invention has been accomplished based on this finding.

DETAILED DESCRIPTION OF THE INVENTION

Problems to be Solved by the Invention

Therefore, the present invention intends to provide a highly enantioselective chiral bifunctional organocatalyst and a method for preparing the chiral organocatalyst.

The present invention also intends to provide a method for producing an unnatural γ-amino acid from a nitro compound using the chiral organocatalyst.

Means for Solving the Problems

The present invention provides a chiral organocatalyst represented by Formula 1:

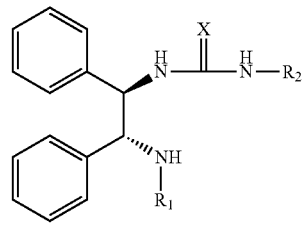

[Formula 1]

The structure and substituents of the chiral organocatalyst represented by Formula 1 will be described below.

The present invention also provides a method for preparing the chiral organocatalyst represented by Formula 1, including (a) reacting (R,R)-1,2-diphenylethylenediamine (DPEN) represented by Formula 2:

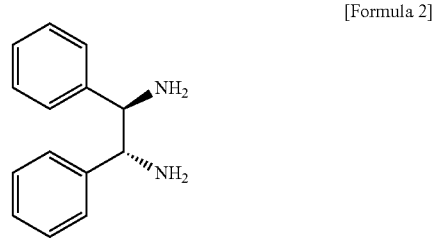 [SMILES: N[C@H](c1ccccc1)[C@H](N)c1ccccc1]

[Formula 2]

with a thiourea.

The present invention also provides a method for producing an unnatural γ-amino acid, including (A) performing a Michael addition reaction of an α,β-unsaturated nitro compound with a malonic acid or malononitrile in the presence of the chiral organocatalyst represented by Formula 1.

Effects of the Invention

The chiral bifunctional organocatalyst of the present invention is highly enantioselective and can be easily synthesized. The use of the chiral organocatalyst enables the production of γ-amino acids with high enantioselectivity in high yield in an economical and simple manner. In addition, even a small amount of the chiral organocatalyst is sufficient for mass production of various unnatural γ-amino acids with R configuration in high optical purity. Therefore, the chiral organocatalyst of the present invention can be widely utilized in various industrial fields, including the pharmaceutical industry.

BRIEF DESCRIPTION OF THE DRAWINGS

FIG. 1 shows the structures of substituted chiral organocatalysts according to exemplary embodiments of the present invention.

FIG. 2 shows a reaction scheme for the synthesis of a monoalkylated thiourea catalyst according to one embodiment of the present invention.

FIG. 3 shows a reaction scheme for the synthesis of an arylated thiourea catalyst according to one embodiment of the present invention.

FIG. 4 shows a reaction scheme for Michael addition according to one embodiment of the present invention.

FIG. 5 shows a reaction scheme for the production of an unnatural γ-amino acid according to one embodiment of the present invention.

FIG. 6 shows a scheme for testing Michael addition reactions using different amounts of different chiral organocatalysts in different solvents according to exemplary embodiments of the present invention.

FIG. 7 shows a scheme for testing Michael addition reactions of different α,β-unsaturated nitro compounds according to exemplary embodiments of the present invention (a) indicates the use of 0.4 ml on a 0.1 mmol scale).

FIG. 8 shows a reaction scheme for the production of an unnatural γ-amino acid according to one embodiment of the present invention.

FIG. 9 shows a reaction scheme for the production of an unnatural γ-amino acid according to one embodiment of the present invention.

BEST MODE FOR CARRYING OUT THE INVENTION

Unless otherwise defined, all technical and scientific terms used herein have the same meaning as commonly understood by one of ordinary skill in the art to which this invention belongs. In general, the nomenclature used herein is well known and commonly employed in the art.

One aspect of the present invention is directed to a chiral organocatalyst represented by Formula 1:

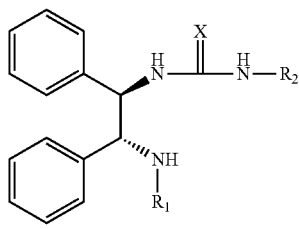

[Formula 1]

wherein X is selected from O, S, P—$R_3$, and N—$R_4$ and $R_1$ to $R_4$ are identical to or different from each other and are each independently selected from hydrogen, deuterium, substituted or unsubstituted $C_1$-$C_{30}$ alkyl, substituted or unsubstituted $C_3$-$C_{30}$ cycloalkyl, substituted or unsubstituted $C_2$-$C_{30}$ heteroaryl, substituted or unsubstituted $C_6$-$C_{30}$ aryl, substituted or unsubstituted $C_6$-$C_{30}$ arylamino, substituted or unsubstituted $C_1$-$C_{30}$ alkoxy, substituted or unsubstituted $C_2$-$C_{30}$ alkoxycarbonyl, substituted or unsubstituted $C_2$-$C_{30}$ alkoxycarbonylamino, substituted or unsubstituted $C_7$-$C_{30}$ aryloxycarbonylamino, substituted or unsubstituted $C_2$-$C_{30}$ alkenyl, substituted or unsubstituted $C_2$-$C_{30}$ alkynyl, substituted or unsubstituted $C_3$-$C_{40}$ silyl, substituted or unsubstituted $C_3$-$C_{40}$ silyloxy, substituted or unsubstituted $C_1$-$C_{30}$ acyl, substituted or unsubstituted $C_1$-$C_{20}$ acyloxy, and substituted or unsubstituted $C_1$-$C_2$ acylamino.

According to a preferred embodiment of the present invention, $R_1$ may be hydrogen, 3-pentyl, $Ph_2CH$ or 3,5-$(CF_3)_2$-$PhCH_2$ and $R_2$ may be phenyl, 3,5-$(CF_3)_2$-Ph, p-tolyl, 4-$CF_3$-Ph, $C_6F_5$, 4-$NO_2$-Ph, 4-CN-Ph, 4-F-Ph, t-butyl or 3,5-$(Me)_2$-Ph.

A further aspect of the present invention is directed to a method for preparing the chiral organocatalyst represented by Formula 1, including (a) reacting (R,R)-1,2-diphenylethylenediamine (DPEN) represented by Formula 2:

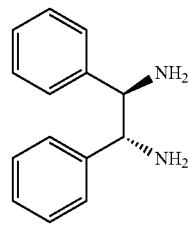

[Formula 2]

with a thiourea.

Another aspect of the present invention is directed to a method for producing an unnatural γ-amino acid, including (A) performing a Michael addition reaction of an α,β-unsaturated nitro compound with a malonic acid or malononitrile in the presence of the chiral organocatalyst represented by Formula 1.

According to a preferred embodiment of the present invention, the Michael addition reaction is performed in the absence or presence of water or an organic solvent, more preferably in the absence or presence of water and affords a nitrostyrene.

The water is generally a solvent called water and may be, for example, cosmetic water, hexagonal water, hot vacuum water, distilled water, single-distilled water, double-distilled water, triple-distilled water, hydrogen water, extraction water, salt-containing water, drinking water, seawater, salt water, brackish water, mineral water, seltzer, bedrock water, spring water, groundwater, deep water, soft water, tap water, hard water, ionized water, electrolyzed water or carbonated water but is not limited thereto. The organic solvent is also not particularly limited.

The method of the present invention may further include synthesizing a pyrrolidinone from the Michael adduct wherein the pyrrolidinone is represented by Formula 3-1 or 3-2:

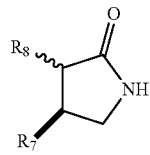

[Formula 3-1]

wherein $R_7$ and $R_8$ are identical to or different from each other and are each independently selected from hydrogen, deuterium, substituted or unsubstituted $C_1$-$C_{30}$ ketone, substituted or unsubstituted $C_1$-$C_{30}$ nitro, substituted or unsubstituted $C_1$-$C_{30}$ halogen, substituted or unsubstituted $C_1$-$C_{30}$ cyano, substituted or unsubstituted $C_1$-$C_{30}$ ester, substituted or unsubstituted $C_1$-$C_{30}$ alkyl, substituted or unsubstituted $C_3$-$C_{30}$ cycloalkyl, substituted or unsubstituted $C_2$-$C_{30}$ heteroaryl, substituted or unsubstituted $C_6$-$C_{30}$ aryl, substituted or unsubstituted $C_6$-$C_{30}$ arylamino, substituted or unsubstituted $C_1$-$C_{30}$ alkoxy, substituted or unsubstituted $C_2$-$C_{30}$ alkoxycarbonyl, substituted or unsubstituted $C_2$-$C_{30}$ alkoxycarbonylamino, substituted or unsubstituted $C_7$-$C_{30}$ aryloxycarbonylamino, substituted or unsubstituted $C_2$-$C_{30}$ alkenyl, substituted or unsubstituted $C_2$-$C_{30}$ alkynyl, substituted or unsubstituted $C_3$-$C_{40}$ silyl, substituted or unsubstituted $C_3$-$C_{40}$ silyloxy, substituted or unsubstituted $C_1$-$C_{30}$ acyl, substituted or unsubstituted $C_1$-$C_{20}$ acyloxy, and substituted or unsubstituted $C_1$-$C_2$ acylamino,

[Formula 3-2]

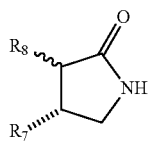

wherein $R_7$ and $R_8$ are as defined in Formula 3-1.

The method of the present invention may further include treating the pyrrolidinone with hydrochloric acid to produce an unnatural γ-amino acid represented by Formula 4-1 or 4-2:

[Formula 4-1]

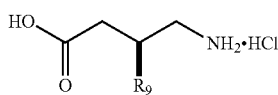

wherein $R_9$ is selected from hydrogen, deuterium, substituted or unsubstituted $C_1$-$C_{30}$ ketone, substituted or unsubstituted $C_1$-$C_{30}$ nitro, substituted or unsubstituted $C_1$-$C_{30}$ halogen, substituted or unsubstituted $C_1$-$C_{30}$ cyano, substituted or unsubstituted $C_1$-$C_{30}$ ester, substituted or unsubstituted $C_1$-$C_{30}$ alkyl, substituted or unsubstituted $C_3$-$C_{30}$ cycloalkyl, substituted or unsubstituted $C_2$-$C_{30}$ heteroaryl, substituted or unsubstituted $C_6$-$C_{30}$ aryl, substituted or unsubstituted $C_6$-$C_{30}$ arylamino, substituted or unsubstituted $C_1$-$C_{30}$ alkoxy, substituted or unsubstituted $C_2$-$C_{30}$ alkoxycarbonyl, substituted or unsubstituted $C_2$-$C_{30}$ alkoxycarbonylamino, substituted or unsubstituted $C_7$-$C_{30}$ aryloxycarbonylamino, substituted or unsubstituted $C_2$-$C_{30}$ alkenyl, substituted or unsubstituted $C_2$-$C_{30}$ alkynyl, substituted or unsubstituted $C_3$-$C_{40}$ silyl, substituted or unsubstituted $C_3$-$C_{40}$ silyloxy, substituted or unsubstituted $C_1$-$C_{30}$ acyl, substituted or unsubstituted $C_1$-$C_{20}$ acyloxy, and substituted or unsubstituted $C_1$-$C_2$ acylamino,

[Formula 4-2]

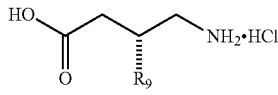

wherein $R_9$ is as defined in Formula 4-1.

The unnatural γ-amino acid of Formula 4-1 wherein $R_9$ is a phenyl group may be represented by Formula 5-1:

[Formula 5-1]

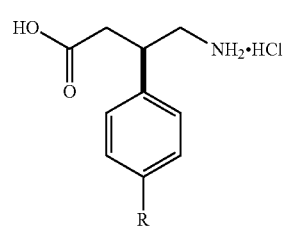

wherein R is hydrogen or halogen.

The unnatural γ-amino acid of Formula 4-2 wherein $R_9$ is a phenyl group may be represented by Formula 5-2:

[Formula 5-2]

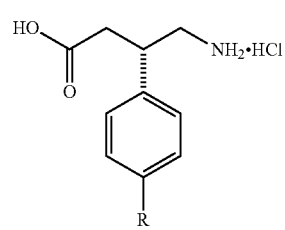

wherein R is as defined in Formula 5-1.

The unnatural γ-amino acid of Formula 5-1 or 5-2 wherein R is hydrogen is phenibut as a sleep inducer. The unnatural γ-amino acid of Formula 5-1 or 5-2 wherein R is chlorine is baclofen as a muscle relaxant.

MODE FOR CARRYING OUT THE INVENTION

The present invention will be explained in more detail with reference to the following examples. It will be obvious to one of ordinary skill in the art that these examples are provided for illustrative purposes only and are not intended to limit the scope of the present invention. Therefore, the substantial scope of the present invention is defined by the appended claims and their equivalents.

Example 1: Preparation of Chiral Organocatalysts 1-1: Backbone Structure of Chiral Organocatalysts (R,R)-1,2-diphenylethylenediamine (DPEN) of Formula 2 was used as a backbone structure for preparing chiral organocatalysts:

[Formula 2]

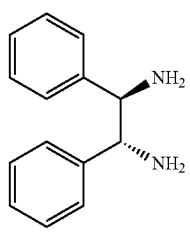

The backbone structure contains amino groups at the C-1 and C-2 positions and has chirality at the C-1 and C-2 positions.

1-2: Preparation of Chiral Organocatalysts

The backbone structure was allowed to react with a thiourea to prepare a chiral organocatalyst of Formula 1 (FIG. 1).

[Formula 1]

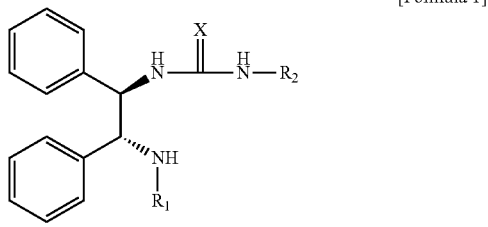

The chiral organocatalyst of Formula 1 has a structure in which the $R_2$ moiety derived from the thiourea is attached to the backbone structure. When $R_2$ is an electron withdrawing group, the reaction yield is predicted to be high in view of the characteristics of the $R_2$ moiety. The chiral organocatalyst is predicted to be highly enantioselective due to the presence of the $R_1$-substituted amino group at the C-2 position.

Synthesis of Monoalkylated Thiourea Catalysts

To a solution of (R,R)-1,2-diphenylethylenediamine (1.0 equiv.) in toluene (0.1 M) was added a solution of 3-pentanone (1.1 equiv.) and $MgSO_4$. The mixture was refluxed for 48 h. Then, $MgSO_4$ was removed by filtration through Celite and the mixture concentrated in vacuo. After addition of $NaBH_4$ (4.0 equiv.) and ethanol, the resulting mixture was stirred at room temperature for 1 h. The reaction was quenched with 1 N NaOH solution and the reaction mixture was extracted with ethyl acetate. The combined organic extracts were washed with brine, dried over $MgSO_4$, and concentrated in vacuo. The residue was purified by chromatography on a silica-gel column (methanol/methylene chloride, 1:20). To monoalkylated DPEN (1.0 equiv.) in $CH_2Cl_2$ (0.1 M) was added thiourea (1.1 equiv.). The mixture was stirred at room temperature for 1 h and purified by flash column chromatography on silica gel with EA/hexane (1:5) to give the pure amide product (quantitative yield) as a white, foamy solid (FIG. 3).

Synthesis of Arylated Thiourea Catalysts

To a suspension of (R,R)-1,2-diphenylethylenediamine (1.0 equiv.) in toluene (0.5 M) was added thiourea (1.0 equiv.) at 0° C. The mixture was stirred for 30 sec. The reaction mixture was concentrated in vacuo and purified by flash column chromatography on silica gel with methanol/methylene chloride (1:20). To thiourea-substituted DPEN (1.0 equiv.) in $CH_2Cl_2$ (0.1 M) was added an alkyl ketone (1.1 equiv.). The mixture was stirred at room temperature for 1 h. After addition of $NaBH_4$ (2.0 equiv.) and ethanol at 0° C., the resulting mixture was stirred at room temperature for 1 h. The reaction mixture was filtered a pad of celite and extracted with ethyl acetate. The combined organic extracts were washed with brine, dried over $MgSO_4$, and concentrated in vacuo. The residue was purified by chromatography on a silica-gel column (methanol/methylene chloride, 1:20) to give the pure amide product (quantitative yield) as a brown, foamy solid (FIG. 3).

In FIG. 1 and Table 1, 1a indicates the chiral organocatalyst of Formula 1 wherein $R_1$ is hydrogen and $R_2$ is phenyl (ph), 1b indicates the chiral organocatalyst of Formula 1 wherein $R_1$ is hydrogen and $R_2$ is 3,5-$(CF_3)_2$-Ph, 1e indicates the chiral organocatalyst of Formula 1 wherein $R_1$ is 3-pentyl and $R_2$ is p-tolyl, 1d indicates the chiral organocatalyst of Formula 1 wherein $R_1$ is 3-pentyl and $R_2$ is 3,5-$(CF_3)_2$-Ph, 1e indicates the chiral organocatalyst of Formula 1 wherein $R_1$ is 3-pentyl and $R_2$ is 4-$CF_3$-Ph, 1f indicates the chiral organocatalyst of Formula 1 wherein $R_1$ is 3-pentyl and $R_2$ is $C_6F_5$, 1g indicates the chiral organocatalyst of Formula 1 wherein $R_1$ is 3-pentyl and $R_2$ is 4-$NO_2$-Ph, 1h indicates the chiral organocatalyst of Formula 1 wherein $R_1$ is 3-pentyl and $R_2$ is 4-NC-Ph, 1i indicates the chiral organocatalyst of Formula 1 wherein $R_1$ is 3-pentyl and $R_2$ is 4-F-Ph, 1j indicates the chiral organocatalyst of Formula 1 wherein $R_1$ is $Ph_2CH$ and $R_2$ is 3,5-$(CF_3)_2$-Ph, 1k indicates the chiral organocatalyst of Formula 1 wherein $R_1$ is $Ph_2CH$ and $R_2$ is t-butyl, 1l indicates the chiral organocatalyst of Formula 1 wherein $R_1$ is $Ph_2CH$ and $R_2$ is 4-$CF_3$-Ph, 1m indicates the chiral organocatalyst of Formula 1 wherein $R_1$ is 3,5-$(CF_3)_2$-Ph-$CH_2$ and $R_2$ is 3,5-$(CF_3)_2$-Ph, and 1n indicates the chiral organocatalyst of Formula 1 wherein $R_1$ is 3,5-$(CF_3)_2$-Ph-$CH_2$ and $R_2$ is 3,5-$(CF_3)_2$-Ph.

TABLE 1

| Chiral organocatalyst | Chemical name |
|---|---|
| 1a | 1-[(1R,2R)-2-Amino-1,2-diphenylethyl]-3-phenylthiourea |
| 1b | 1-[(1R,2R)-2-Amino-1,2-diphenylethyl]-3-[3,5-Bis(trifluoromethyl)phenyl]thiourea |
| 1c | 1-[(1R,2R)-2-(Pentan-3-ylamino)-1,2-diphenylethyl]-3-(p-tolyl)thiourea |
| 1d | 1-[3,5-Bis(trifluoromethyl)phenyl]-3-[(1R,2R)-2-(pentan-3-ylamino)-1,2-diphenylethyl]thiourea |
| 1e | 1-[(1R,2R)-2-(Pentan-3-ylamino)-1,2-diphenylethyl]-3-[4-(trifluoromethyl)phenyl]thiourea |
| 1f | 1-[(1R,2R)-2-(Pentan-3-ylamino)-1,2-diphenylethyl]-3-(perfluorophenyl)thiourea |
| 1g | 1-(4-Nitrophenyl)-3-[(1R,2R)-2-(pentan-3-ylamino)-1,2-diphenylethyl]thiourea |
| 1h | 1-(4-Cyanophenyl)-3-[(1R,2R)-2-(pentan-3-ylamino)-1,2-diphenylethyl]thiourea |
| 1i | 1-(4-Fluorophenyl)-3-[(1R,2R)-2-(pentan-3-ylamino)-1,2-diphenylethyl]thiourea |

TABLE 1-continued

| Chiral organocatalyst | Chemical name |
|---|---|
| 1j | 1-((1R,2R)-2-(benzhydrylamino)-1,2-diphenylethyl)-3-(3,5-bis(trifluoromethyl)phenyl)thiourea |
| 1k | 1-((1R,2R)-2-(benzhydrylamino)-1,2-diphenylethyl)-3-tert-butylthiourea |
| 1l | 1-((1R,2R)-2-(benzhydrylamino)-1,2-diphenylethyl)-3-(4-(trifluoromethyl)phenyl)th-iourea |
| 1m | 1-((1R,2R)-2-(3,5-bis(trifluoromethyl)benzylamino)-1,2-diphenylethyl)-3-(3,5-bis(trifluoromethyl)phenyl)thiourea |
| 1n | 1-((1R,2R)-2-(3,5-dimethylbenzylamino)-1,2-diphenylethyl)-3-(3,5-dimethylphenyl)th-iourea |

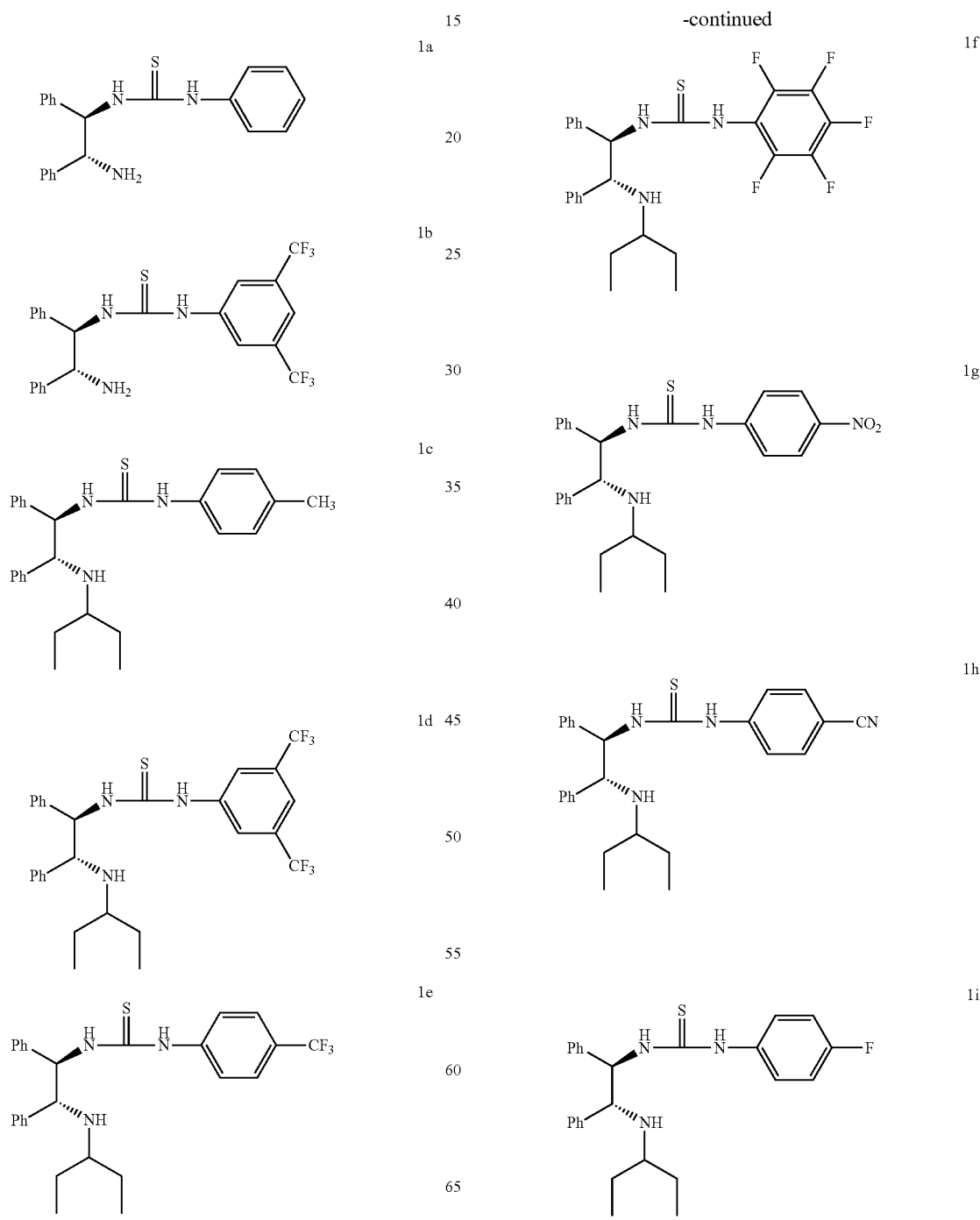

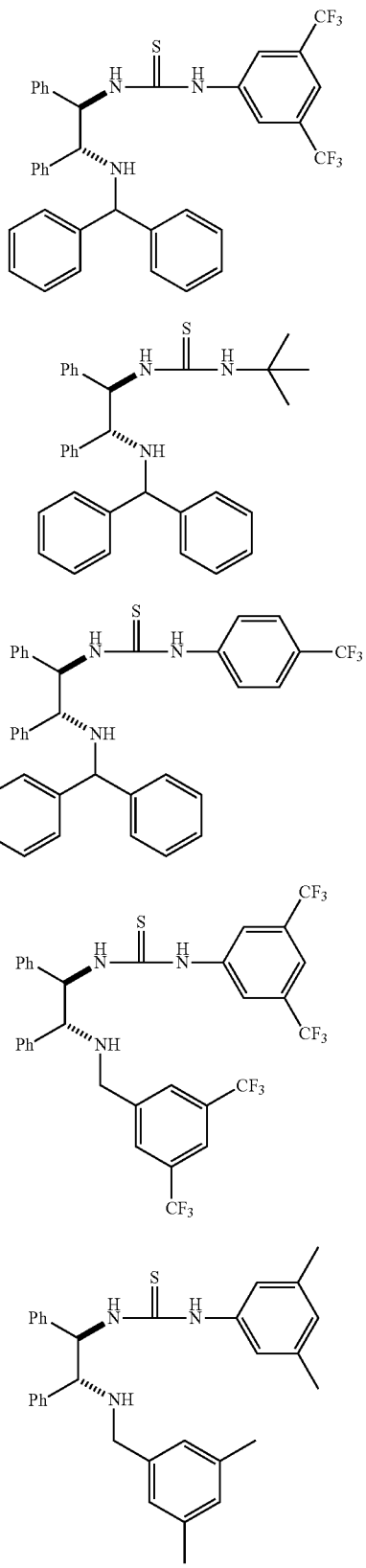

The results of NMR analysis for the chiral organocatalysts 1a to 1n are as follows:

(1a) 94% yield; $[\alpha]_D^{20}$=+62.0 (c=0.02, $CH_2Cl_2$); $^1$H NMR (300 MHz, $CDCl_3$) δ 7.76 (s, 1H), 7.54~7.19 (m, 15H), 5.54 (s, 1H), 4.42 (d, 1H, J=5 Hz), 1.35 (br s, 1H); $^{13}$C NMR (100 MHz, DMSO-$d_6$) δ 182.09, 134.48, 133.93, 129.89, 128.70, 128.10, 127.91, 127.15, 126.94, 126.82, 126.74, 126.23, 125.59, 125.24, 122.98, 63.07, 59.09; IR (KBr) 3287.86, 3027.84, 1521.63, 1241.99, 1072.28, 939.20, 698.13 cm$^{-1}$; HRMS (FAB$^+$) for $C_{21}H_{22}N_3S$ [M+H]$^+$ Calcd: 348.4918, Found: 348.1534.

(1b) $[\alpha]_D^{25}$=+13.5 (c 1.00, $CH_3Cl$); $^1$H NMR (300 MHz, DMSO-$d_6$) δ 10.70 (s, 1H), 8.32 (s, 2H), 7.71 (s, 1H), 7.22~7.43 (m, 13H), 5.57 (d, J=3 Hz, 1H), 4.44 (d, J=3 Hz, 1H) ppm; $^{13}$C NMR (100 MHz, DMSO-$d_6$) δ 180.80, 143.41, 142.67, 130.94, 130.62, 128.81, 128.61 127.75, 127.57, 127.51, 125.25, 122.54, 121.68, 116.40, 63.86, 60.06 ppm; IR (KBr) 3305, 3032, 2963, 1652, 1601, 1557, 1383, 1277, 1262, 803, 700 cm$^{-1}$; HRMS (FAB$^+$) for $C_{22}H_2N_4S$ [M+H]$^+$ Calcd: 372.1487, Found: 372.1456.

(1c) 86% yield; $[\alpha]_D^{20}$=+0.19 (c=1.00, $CH_2Cl_2$); $^1$H NMR (300 MHz, DMSO-$d_6$) δ 9.76 (s, 1H), 7.89 (d, J=7.0 Hz, 1H), 7.32~7.18 (m, 14H), 5.44 (s, 1H), 4.08 (d, J=5.1 Hz, 1H), 2.29 (s, 2H), 2.02 (s, 1H), 1.39 (s, 1H), 1.20~1.06 (m, 4H), 0.68 (t, J=7.5 Hz, 3H), 0.41 (t, J=7.1 Hz, 3H); $^{13}$C NMR (100 MHz, DMSO-$d_6$) δ 181.04, 141.83, 141.55, 136.71, 134.88, 130.03, 128.67, 128.51, 127.49, 127.40, 124.67, 64.28, 63.77, 55.84, 26.71, 24.02, 21.20, 10.94, 8.30; IR (KBr) 3180.2, 2958.4, 1948.8, 1510.1, 1240.1, 821.6, 700.1, 565.1 cm$^{-1}$; HRMS (FAB$^+$) for $C_{27}H_{34}N_3S$ [M+H]$^+$ Calcd: 432.2473, Found: 432.6537, pattern 432.5, 345.3, 266.4, 176.3, 106.01.

(1d) 90% yield; $[\alpha]_D^{20}$=+0.31 (c=0.11, $CH_2Cl_2$); $^1$H NMR (300 MHz, DMSO-$d_6$) δ 10.5 (br, 1H), 8.30 (s, 2H), 7.74 (s, 1H), 7.40~7.19 (m, 10H), 5.57 (br, 1H), 4.18 (d, J=4.9 Hz, 1H), 2.09 (m, 1H), 1.24~1.20 (m, 4H), 0.75 (t, J=7.1 Hz, 3H), 0.50 (t, J=6.0 Hz, 3H); $^{13}$C NMR (100 MHz, DMSO-$d_6$) δ 181.10, 142.49, 140.88, 130.96, 130.64, 128.70, 128.59, 128.56, 127.60, 125.22, 122.52, 122.19, 116.70, 64.34, 63.62, 56.48, 26.64, 23.90, 10.98, 8.54; IR (KBr) 3239.9, 2964.2, 1471.5, 1278.6, 1135.9, 885.2, 700.1 cm$^{-1}$; HRMS (FAB$^+$) for $C_{28}H_{30}F_6N_3S$ [M+H]$^+$ Calcd: 554.2065, Found: 554.2065.

(1e) 88% yield; $[\alpha]_D^{20}$=+45.5 (c=0.02, $CH_2Cl_2$); $^1$H NMR (300 MHz, DMSO-$d_6$) δ 10.2 (br s, 1H), 8.41 (br s, 1H), 7.79 (d, J=8.0 Hz, 2H), 7.64 (d, J=8.5 Hz, 2H), 7.35~7.15 (m, 10H), 5.53 (br s, 1H), 4.13 (d, J=5.5 Hz, 1H), 2.07 (m, 1H), 1.30~1.15 (m, 4H), 0.73 (t, J=7.1 Hz, 3H), 0.49 (t, J=6.9 Hz, 3H); $^{13}$C NMR (100 MHz, DMSO-$d_6$) δ 180.91, 143.97, 141.18, 128.64, 128.52, 127.69, 127.48, 126.29, 122.41, 64.43, 63.71, 56.32, 26.68, 23.98, 10.98, 8.53; IR(KBr) 3205.3, 2962.3, 1945.9, 1741.5, 1517.8, 1324.9, 1245.9, 1066.5, 840.9, 700.1, 597.9 cm$^{-1}$; HRMS (FAB$^+$) for $C_{27}H_{31}F_3N_3S$[M+H]$^+$ Calcd: 486.2191, Found: 486.2190.

(1f) 89% yield; $[\alpha]_D^{20}$=+80.4 (c=0.02, $CH_2Cl_2$); $^1$H NMR (300 MHz, DMSO-$d_6$) δ 9.47 (s, 1H), 8.61 (s, 1H), 7.30~7.15 (m, 10H), 5.48 (br s, 1H), 4.13 (d, J=6.1 Hz, 1H), 2.08 (m, 1H), 1.54 (br, 1H), 1.30~1.14 (m, 4H), 0.74 (t, J=7.4 Hz, 3H), 0.55 (t, J=6.3 Hz, 3H); $^{13}$C NMR (100 MHz, DMSO-$d_6$) δ 183.63, 145.82, 143.43, 141.90, 140.77, 139.01, 138.84, 136.56, 129.39, 128.61, 128.43, 127.68, 127.60, 115.93, 64.77, 64.53, 56.37, 26.72, 24.16, 10.86, 8.58; IR (KBr) 3299.8, 2964.2, 1525.5, 1344.2, 1145.6, 991.3, 912.2, 700.1, 605.6 cm$^{-1}$; HRMS (FAB$^+$) for $C_{26}H_{27}F_5N_3S$ [M+H]$^+$ Calcd: 508.1846, Found: 508.1848.

(1g) 89% yield; $[\alpha]_D^{20}$=+37.7 (c=0.02, $CH_2Cl_2$); $^1$H NMR (300 MHz, DMSO-$d_6$) δ 10.5 (s, 1H), 8.16 (m, 2H), 7.90 (d, J=9.1 Hz, 2H), 7.37~7.15 (m, 10H), 5.54 (br s, 1H), 4.16 (d, J=5.5 Hz, 1H), 2.07 (m, 1H), 1.30~1.15 (m, 4H), 0.75 (t, J=7.4 Hz, 3H), 0.50 (t, J=7.4 Hz, 3H); $^{13}$C NMR (100 MHz, DMSO-d$_6$) δ 180.51, 146.95, 142.46, 141.92, 140.92, 128.68, 128.56, 127.72, 125.16, 120.92, 64.35, 63.80, 56.35, 55.59, 26.70, 23.96, 11.03, 8.61; IR (KBr) 3330.5, 2960.2, 2599.6, 2456.4, 2345.0, 1951.6, 1743.3, 1496.5, 1346.1, 1110.8, 1072.2, 852.4, 700.0, 586.3 cm$^{-1}$; HRMS (FAB$^+$) for C$_{26}$H$_{31}$N$_4$O$_2$S [M+H]$^+$ Calcd: 463.2168, Found: 463.2165.

(1h) 69% yield; $[\alpha]_D^{20}$=+55.5 (c=0.02, CH$_2$Cl$_2$); $^1$H NMR (300 MHz, DMSO-d$_6$) δ 10.3 (br s, 1H), 8.54 (br s, 1H), 7.84~7.72 (m, 4H), 7.35~7.17 (m, 10H), 5.54 (br s, 1H), 4.14 (d, J=5.2 Hz, 1H), 2.07 (br s, 1H), 1.56 (br s, 1H), 1.21 (m, 4H), 0.74 (t, J=7.4 Hz, 3H), 0.49 (t, J=6.9 Hz, 3H); $^{13}$C NMR (100 MHz, DMSO-d$_6$) δ 180.62, 144.83, 141.92, 141.05, 133.40, 128.67, 128.33, 127.68, 127.64, 127.51, 121.76, 119.76, 105.41, 64.41, 63.72, 60.43, 56.33, 26.74, 23.98, 21.42, 14.74, 11.02, 8.56; IR (KBr) 3317.0, 2960.2, 2360.4, 2225.5, 1949.7, 1739.5, 1508.1, 1315.2, 1176.4, 1072.2, 837.0, 700.0, 545.8 cm$^{-1}$; HRMS (FAB$^+$) for C$_{27}$H$_{31}$N$_4$S [M+H]$^+$ Calcd: 443.2269, Found: 443.2271.

(1i) 84% yield; $[\alpha]_D^{20}$=+17.9 (c=0.02, CH$_2$Cl$_2$); $^1$H NMR (300 MHz, DMSO-d$_6$) δ 9.83 (s, 1H), 8.00 (d, J=6.7 Hz, 1H), 7.48~7.43 (m, 2H), 7.31~7.16 (m, 11H), 5.46 (br s, 1H), 4.09 (d, J=5.22 Hz, 1H), 2.03 (br s, 1H), 1.44 (br s, 1H), 1.14 (m, 4H), 0.70 (t, J=10.1, 3H), 0.44 (t, J=7.0 Hz, 3H); $^{13}$C NMR (100 MHz, DMSO-d$_6$) δ 181.42, 161.03, 158.62, 141.90, 141.44, 135.97, 128.65, 128.51, 127.57, 127.42, 126.49, 116.13, 115.90, 64.39, 63.76, 56.03, 26.72, 24.02, 10.98, 8.39; IR (KBr) 3193.7, 2962.3, 1889.9, 1511.9, 1218.8, 848.6, 701.9, 555.42 cm$^{-1}$; HRMS (FAB$^+$) for C$_{26}$H$_{31}$FN$_3$S[M+H]$^+$ Calcd: 436.6172, Found: 436.2223. pattern 436.5, 349.3, 266.4, 176.3, 106.1.

(1j) 95% yield; $[\alpha]_D^{20}$=+0.39 (c=0.16, CH$_2$Cl$_2$); $^1$H NMR (400 MHz, DMSO-d$_6$) δ 7.82~7.09 (m, 23H), 5.72 (s, 1H), 3.98 (s, 1H), 3.35 (s, 1H), 2.47 (br, 1H); $^{13}$C NMR (100 MHz, DMSO-d$_6$) δ 181.06, 156.63, 153.35, 143.36, 142.03, 141.31, 138.68, 129.48, 129.34, 126.90, 125.59, 123.65, 122.55, 122.14, 70.83, 65.14, 55.50; IR (KBr) 3239.9, 2964.2, 1471.5, 1278.6, 1135.9, 885.2, 700.1 cm$^{-1}$; HRMS (EI$^+$) for C$_{28}$H$_{30}$F$_6$N$_3$S [M+H]$^+$ Calcd: 649.1986, Found: 649.1932.

(1k) 93% yield; $[\alpha]_D^{20}$=+115 (c 0.17, CH$_2$Cl$_2$); $^1$H NMR (400 MHz, DMSO-d$_6$) δ 7.61~7.03 (m, 20H), 4.13 (q, 3H), 2.92 (s, 9H), 1.76 (br, 2H); IR(KBr) 3679.6, 2978.4, 1414.3, 1262.8, 1059.4, 886.1, 735.0 cm$^{-1}$; HRMS(EI$^+$) for C$_{32}$H$_{35}$N$_3$S [M+H]$^+$ Calcd: 493.2552, Found: 493.2587.

(1k) 89% yield; $[\alpha]_D^{20}$=+124 (c 0.10, CH$_2$C$_{12}$); $^1$H NMR (300 MHz, DMSO-d$_6$) δ 9.44 (br, 1H), 7.77~7.10 (m, 26H), 4.90 (s, 1H), 4.82 (s, 2H), 1.92 (s, 1H); IR(KBr) 3679.5, 3352.2, 2985.3, 1402.4, 1265.9, 1065.7, 726.8 cm$^{-1}$; HRMS (FAB$^+$) for C$_{35}$H$_3$F$_3$N$_3$S [M+H]$^+$ Calcd: 581.2113, Found: 581.2133.

(1m) 93% yield; $[\alpha]_D^{20}$=+0.45 (c=0.11, CH$_2$Cl$_2$); $^1$H NMR (500 MHz, DMSO-d$_6$) δ 7.61 (br, 3H), 7.39~7.29 (m, 16H), 4.54 (s, 4H); $^{13}$C NMR (100 MHz, DMSO-d$_6$) δ 171.58, 157.99, 142.12, 131.46, 134.14, 129.17, 127.28, 125.67, 122.96, 112.29, 89.59, 89.05, 84.78; IR (KBr) 3032.6, 2871.3, 1663.5, 1386.6, 1275.9, 1117.5, 930.2, 700.2 cm$^{-1}$; HRMS (FAB$^+$) for C$_{32}$H$_{23}$F$_{12}$N$_3$S [M+H]$^+$ Calcd: 709.1421, Found: 709.1428.

(1n) 89% yield; $[\alpha]_D^{20}$=+112 (c 0.13, CH$_2$Cl$_2$); $^1$H NMR (500 MHz, DMSO-d$_6$) δ 7.38 (t, 6H), 7.32 (d, 2H), 7.27 (d, 4H), 7.00 (s, 4H), 4.54 (s, 4H), 2.21 (s, 12H), 1.25 (br, 1H); $^{13}$C NMR (100 MHz, DMSO-d$_6$) δ 167.08, 157.71, 156.95, 143.07, 138.05, 131.22, 129.00, 128.93, 127.09, 127.03, 123.43, 118.64, 112.63, 70.28, 68.05, 67.38, 21.63; IR(KBr) 3155.0, 2960.2, 2360.4, 1951.6, 1735.6, 1469.5, 1294.0, 1241.9, 1006.7, 837.0, 700.0, 572.8 cm$^{-1}$; HRMS(FAB$^+$) for C$_{26}$H$_{30}$F$_2$N$_3$S[M+H]$^+$ Calcd: 454.2129, Found: 454.2133.

Example 2: Production of Unnatural γ-Amino Acids Using the Chiral Organocatalysts A Michael addition reaction of an α,β-unsaturated nitro compound with a dialkyl malonate or malononitrile was performed using each of the chiral organocatalysts prepared in Example 1. The Michael addition reaction was completed within 24 h, affording a nitrostyrene in a yield of 91-99% and an enantioselectivity of 91-99%. Applied compounds were synthesized using the Michael adduct. NiCl$_2$.6H$_2$O.NaBH$_4$ was added to a 4-Cl-substituted nitrostyrene as the Michael adduct. As a result of the reaction, the nitro group was reduced and cyclization occurred to form a 2-pyrrolidinone having an ethyl ester group, represented by Formula 3-1 or 3-2:

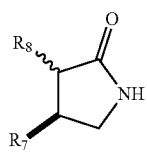

[Formula 3-1]

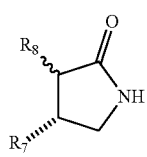

[Formula 3-2]

As a result of the subsequent reaction, the carboxyl group was removed to form a 2-pyrrolidinone. The 2-pyrrolidinone was treated with 6 N HCl to synthesize an unnatural γ-amino acid of Formula 4-1 or 4-2:

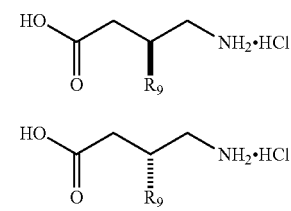

[Formula 4-1]

[Formula 4-2]

The unnatural γ-amino acid of Formula 4-1 or 4-2 wherein R$_9$ is Cl-substituted phenyl is baclofen and the unnatural γ-amino acid of Formula 4-1 or 4-2 wherein R$_9$ is unsubstituted phenyl is phenibut (FIGS. 4 and 5).

Specifically, trans-β-nitrostyrene (1.0 equiv.) as the α,β-unsaturated nitro compound was mixed with malononitrile (2.0 equiv.) in the presence of the chiral organocatalyst 1m (0.1-0.001 mol %) prepared in Example 1 in water (0.4 ml) as a solvent. The mixture was stirred at room temperature. The reaction conversion was monitored by TLC. After completion of the reaction, 6 N HCl was added to the reaction mixture, followed by heating at 65° C. for 2 h. The resulting mixture was cooled to room temperature, added with a dialkyl carbonate (1.5 equiv.), and heated with stirring at 100° C. for 3 h. Thereafter, the homogeneous reaction mixture was cooled to room temperature, poured into a 10% aqueous solution of NaHCO₃, and added with ethyl acetate (0.2 ml). This solution was washed twice with water (2×1.0 mL), dried over magnesium sulfate, and concentrated to afford the desired product. The product was purified by chromatography on a silica-gel column (hexane/methylene chloride, 2:1) (2a-2m in Table 2). Under an argon atmosphere, NaBH₄ (10 equiv.) was added to a suspension of the Michael adduct (1.0 equiv., >99% ee) and NiCl₂.6H₂O (1.0 equiv.) in MeOH (8.0 ml) at 0° C. The mixture was stirred at room temperature for 7.5 h. The reaction was quenched with NH₄Cl and the reaction mixture was diluted with CHCl₃. The organic layer was separated, dried over MgSO₄, filtered, and concentrated in vacuo. The residue was purified by chromatography on silica gel (MeOH/CHCl₃₌₁/₂₀ as the eluent) to afford the desired product as a colorless powder (2n and 2o in Table 2). The product 2n or 2o (1.0 equiv.) in 6 N HCl (2.7 ml) was refluxed at 100° C. After 12 h, the reaction mixture was concentrated in vacuo to afford (R)-(−)-baclofen and phenibut (2p and 2q in Table 2, 97-98%) as colorless solids.

TABLE 2

| Product | Chemical name |
|---|---|
| 2a | (R)-Dimethyl 2-(2-nitro-1-phenylethyl)malonate |
| 2b | (R)-Diethyl 2-(2-nitro-1-phenylethyl)malonate |
| 2c | (R)-Diisopropyl 2-(2-nitro-1-phenylethyl)malonate |
| 2d | (R)-Dipropyl 2-(2-nitro-1-phenylethyl)malonate |
| 2e | (R)-Benzyl-2-carbobenzyloxy-4-nitro-3-phenylbutyrate |
| 2f | (R)-dibutyl 2-(2-nitro-1-phenylethyl)malonate |
| 2g | (R)-Diethyl 2-[1-(4-bromophenyl)-2-nitroethyl]malonate |
| 2h | (R)-diethyl 2-(1-(4-chlorophenyl)-2-nitroethyl)malonate |
| 2i | (R)-Diethyl 2-[2-nitro-1-(p-tolyl)ethyl]malonate |
| 2j | (R)-Diethyl 2-[1-(4-hydroxyphenyl)-2-nitroethyl]malonate |
| 2k | (R)-Diethyl 2-[1-(4-methoxyphenyl)-2-nitroethyl]malonate |
| 2l | (R)-Diethyl 2-[1-(2-methoxyphenyl)-2-nitroethyl]malonate |
| 2m | (R)-Diethyl 2-[1-(furan-2-yl)-2-nitroethyl]malonate |
| 2n | (R)-ethyl 2-oxo-4-phenylpyrrolidine-3-carboxylate |
| 2o | (R)-Ethyl 4-(4-chlorophenyl)-2-oxopyrrolidine-3-carboxylate |
| 2p | (R)-4-amino-3-phenyl-butanoic acid hydrochloride |
| 2q | (R)-4-Amino-[3-(4-chlorophenyl)]-butanoic acid hydrochloride |
| 3a | (S)-4-Nitro-1,3-diphenyl-butan-1-one |
| 3b | (S)-3-(4-Chlorophenyl)-4-nitro-1-phenylbutan-1-one |
| 3c | (S)-4-nitro-1-phenyl-3-(p-tolyl)butan-1-one |
| 3d | (S)-3-(4-Bromophenyl)-4-nitro-1-phenylbutan-1-one |
| 3e | (S)-3-(4-Chlorophenyl)-4-nitro-1-phenylbutan-1-one |
| 3f | (S)-3-(4-Methoxyphenyl)-4-nitro-1-phenylbutan-1-one |
| 3g | (S)-3-(2-Methoxyphenyl)-4-nitro-1-phenylbutan-1-one |
| 3h | (S)-3-(Furan-2-yl)-4-nitro-1-phenylbutan-1-one |
| 3i | (S)-Phenyl 4-nitro-3-phenylbutanoate |
| 3j | (S)-Phenyl 3-(4-chlorophenyl)-4-nitrobutanoate |
| 3k | (S)-4-Phenylpyrrolidin-2-one |
| 3l | (R)-4-Phenylpyrrolidin-2-one |
| 3m | (S)-4-(4-Chlorophenyl)pyrrolidin-2-one |
| 3n | (R)-4-(4-Chlorophenyl)pyrrolidin-2-one |
| 3o | (S)-4-Amino-3-phenylbutanoicacid |
| 3p | (S)-4-Amino-3-(4-chlorophenyl)butanoic acid |
| 3q | (S)-2-(2-oxo-4-phenylpyrrolidin-1-yl)acetamide |
| 3r | (R)-2-(2-oxo-4-phenylpyrrolidin-1-yl)acetamide |
| 3s | (S)-2-((R)-2-oxo-4-propylpyrrolidin-1-yl)butanamide |

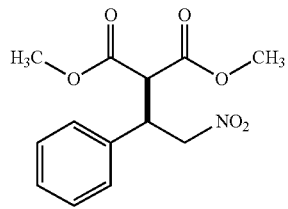

2a

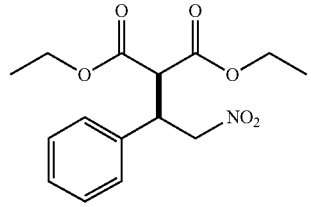

2b

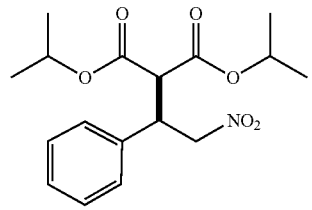

2c

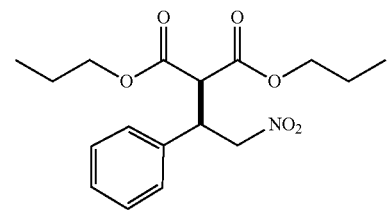

2d

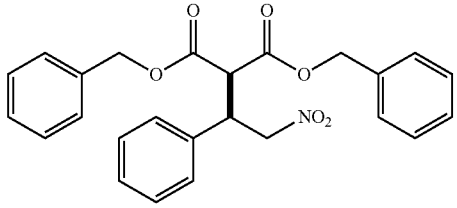

2e

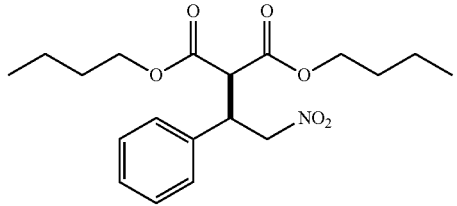

2f

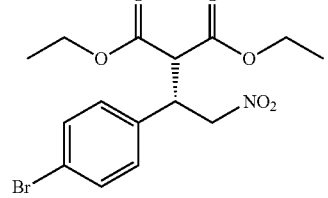

2g

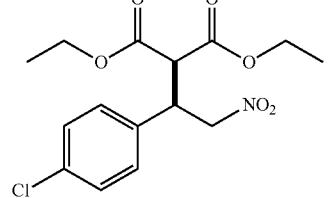

2h

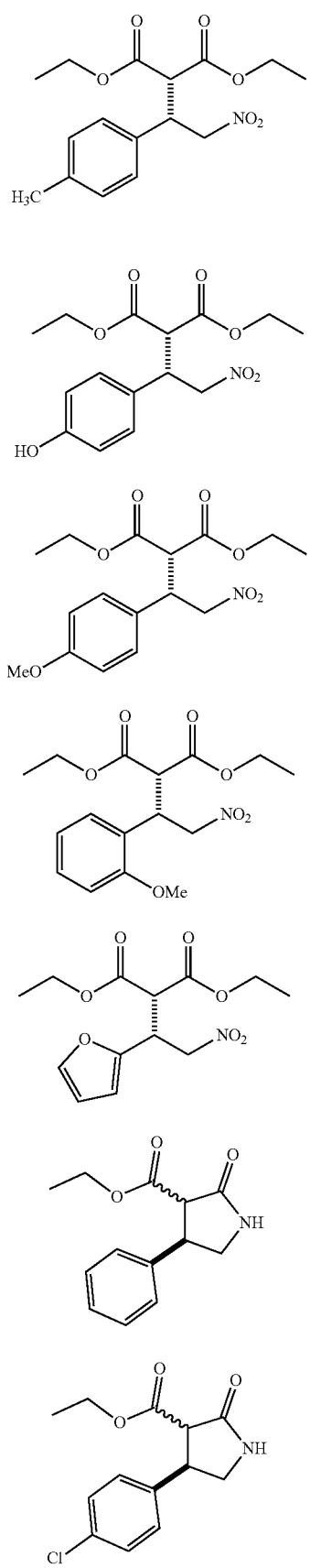
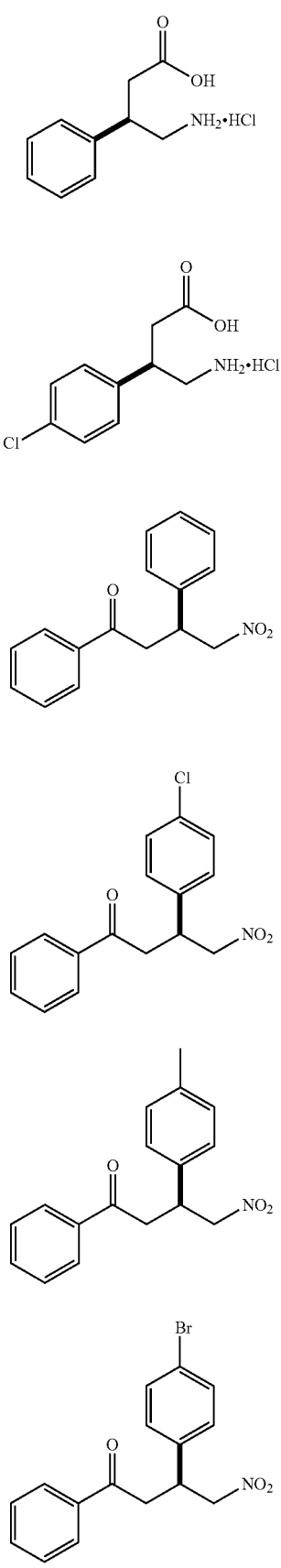

-continued
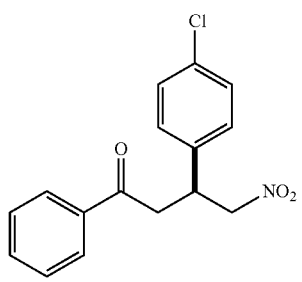
3e
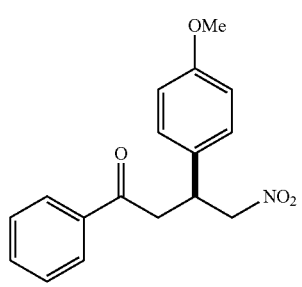
3f
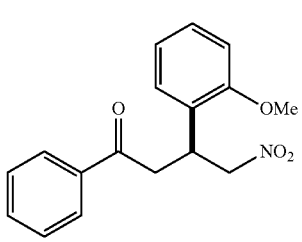
3g
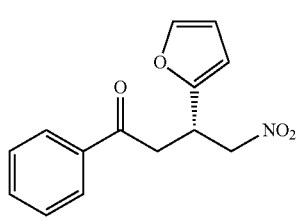
3h
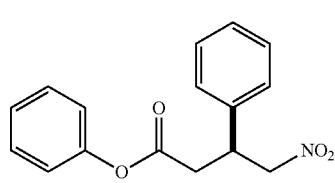
3i
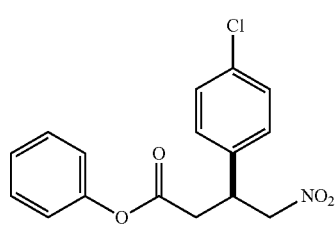
3j
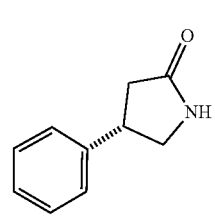
3k
-continued
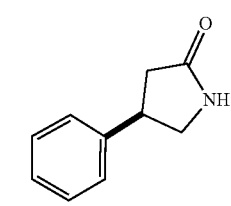
3l
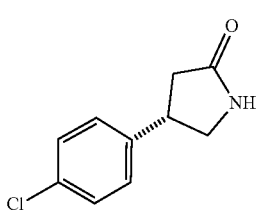
3m
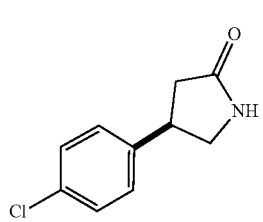
3n
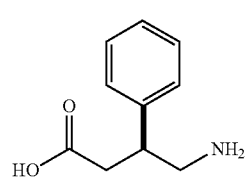
3o
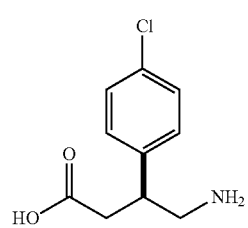
3p
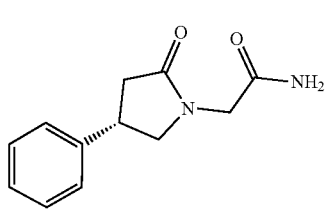
3q
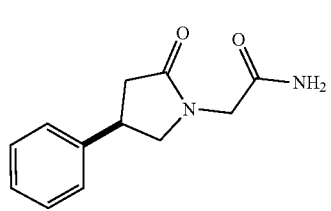
3r -continued

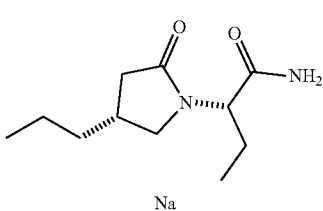

3s

The analytical results of the products 2a to 2q and 3a to 3s are as follows:

(2a) $[\alpha]_D^{20}$=−1.98 (c 1.33, CH$_2$Cl$_2$); $^1$H NMR (300 MHz, CDCl$_3$) δ7.40~7.15 (m, 5H), 5.15~5.03 (m, 1H), 4.93 (dd, J=4.5, 12.8 Hz, 1H), 4.88~4.76 (m, 2H), 4.20 (td, J=4.5, 9.5 Hz, 1H), 3.76 (d, J=9.5 Hz, 1H), 1.24 (d, J=6.1 Hz, 3H), 1.07 (d, J=6.4 Hz, 3H), 1.01 (d, J=6.4 Hz, 3H) ppm; $^{13}$C NMR (100 MHz, CDCl$_3$) δ 167.1, 166.4, 136.3, 128.9, 128.3, 128.2, 77.9, 69.9, 69.5, 55.1, 42.9, 21.5, 21.4, 21.19, 21.17 ppm; IR(KBr) 3030, 2985, 1727, 1557 cm$^{-1}$; HRMS(ESI) for C$_{13}$H$_{16}$N$_1$O$_6$[M+H]$^+$ Calcd: 282.09721, Found: 282.09726; HPLC [Chiralcel AD-H, hexane/2-propanol=95/5, 1.0 mL/min, k=254 nm, retention times: (major) 23.3 min, (minor) 38.0 min].

(2b) $[\alpha]_D^{20}$=−4.61 (c 0.23, CH$_2$Cl$_2$); $^1$H NMR (300 MHz, CDCl$_3$) δ7.30~7.20 (m, 5H), 4.93 (dd, J=4.6, 13.1 Hz, 1H), 4.86 (dd, J=9.2, 13.1 Hz, 1H), 4.24~4.17 (m, 3H), 3.98~3.97 (q, J=7.2 Hz, 2H), 3.81~3.79 (d, J=9.5 Hz, 1H), 1.25 (t, J=7.2 Hz, 3H), 1.03 (t, J=7.2 Hz, 3H) ppm; $^{13}$C NMR (100 MHz, CDCl$_3$) δ 167.4, 166.7, 136.2, 128.8, 128.2, 127.9, 77.6, 62.0, 61.8, 54.9, 42.9, 13.9, 13.6 ppm; IR(KBr) 2989, 2938, 1731, 1557 cm$^{-1}$; HRMS(ESI) for C$_{15}$H$_{20}$N$_1$O$_6$[M+H]$^+$ Calcd: 310.12851, Found: 310.12936; HPLC [Chiralcel AD-H, hexane/ethanol=90/10, 1.0 mL/min, k=254 nm, retention times: (major) 11.5 min, (minor) 15.3 min].

(2c) $[\alpha]_D^{20}$=−1.24 (c 1.00, CH$_2$Cl$_2$); $^1$H NMR (300 MHz, CDCl$_3$) δ7.32~7.22 (m, 5H), 5.10 (dd, J=5.0, 13.1 Hz, 1H), 4.91~4.979 (m, 3H), 4.21~4.19 (m, 1H), 1.25 (d, J=2.0 Hz, 6H), 1.07 (dd, J=2.0, 2.0 Hz, 6H) ppm; $^{13}$C NMR (100 MHz, CDCl$_3$) δ 167.27, 166.54, 136.47, 129.07, 128.34, 127.9, 78.15, 70.15, 69.75, 55.35, 43.14, 21.80, 21.67, 21.48 ppm; IR(KBr) 3029, 2956, 1737, 1558 cm$^{-1}$; HRMS(ESI) for C$_{17}$H$_{24}$N$_1$O$_6$[M+H]$^+$ Calcd: 338.15981 Found: 338.16336; HPLC [Chiralcel AD-H, hexane/2-propanol=95/5, 1.0 mL/min, λ=254 nm, retention times: (major) 14.8 min, (minor) 34.4 min].

(2d) $[\alpha]_D^{20}$=−1.73 (c 0.10, CH$_2$Cl$_2$); $^1$H NMR (300 MHz, CDCl$_3$) δ 7.31~7.22 (m, 5H), 4.92~4.87 (t, J=5.0, 9.5 Hz, 2H), 4.24 (m, 1H), 4.15~4.09 (m, 2H), 3.92~3.83 (dd, s, J=6.6 9.7 Hz, 3H), 1.68~1.61 (m, 2H), 1.49~1.42 (m, 2H), 0.93~0.88 (t, J=7.4, 7.4 Hz, 3H), 0.82~0.77 (t, J=7.4, 7.4 Hz, 3H) ppm; $^{13}$C NMR (100 MHz, CDCl$_3$) δ 167.79, 167.17, 136.46, 129.14, 128.52, 128.17, 77.85, 67.86, 67.65, 55.17, 43.16, 21.97, 21.81, 10.48 ppm; IR(KBr) 3029, 2956, 1737, 1558 cm$^{-1}$; HRMS(ESI) for C$_{17}$H$_{24}$N$_1$O$_6$[M+H]$^+$ Calcd: 338.15981 Found: 338.16336; HPLC [Chiralcel AD-H, hexane/2-propanol=95/5, 1.0 mL/min, λ=254 nm, retention times: (major) 18.4 min, (minor) 38.9 min].

(2e) $[\alpha]_D^{20}$=−3.25 (c 0.10, CH$_2$Cl$_2$); $^1$H NMR (400 MHz, CDCl$_3$) δ 7.33~7.25 (m, 10H), 7.17~7.07 (m, 5H), 5.16 (d, 1H, J=12.2 Hz), 5.18 (d, 1H, JAB=12.2 Hz), 4.93 (S, 1H), 4.84~4.82 (m, 2H), 4.28~4.22 (q, 1H), 3.94 (d, 1H, 9.3 Hz); 13C NMR (100 MHz, CDCl3) δ 167.39, 166.78, 135.14, 134.85, 129.25, 128.90, 128.15, 77.63, 68.04, 67.86, 55.14, 43.16 ppm; IR(KBr) 3068, 3036, 2963, 1736, 1558, 1498, 1456, 1378, 1326, 1286, 1217, 1156, 1003, 975, 908, 562 cm$^{-1}$; HRMS(EI) for C$_{25}$H$_{23}$N$_1$O$_6$[M+H]$^+$ Calcd: 433.1525 Found: 433.1525; HPLC [Chiralcel AD-H, hexane/2-propanol=70/30, 1.0 mL/min, λ=254 nm, retention times: (major) 26.0 min, (minor) 24.1 min].

(2f) $[\alpha]_D^{20}$=−2.55 (c 0.10, CH$_2$Cl$_2$); $^1$H NMR (400 MHz, CDCl$_3$) δ 7.31~7.22 (m, 5H), 4.92~4.87 (t, J=5.0, 9.5 Hz, 2H), 4.24 (m, 1H), 4.15~4.09 (m, 2H), 3.92~3.83 (dd, s, J=6.6 9.7 Hz, 3H), 1.68~1.61 (m, 2H), 1.49~1.42 (m, 2H), 0.93~0.88 (t, J=7.4, 7.4 Hz, 3H), 0.82~0.77 (t, J=7.4, 7.4 Hz, 3H) ppm; $^{13}$C NMR (100 MHz, CDCl$_3$) δ 167.79, 167.17, 136.46, 129.14, 128.52, 128.17, 77.85, 67.86, 67.65, 55.17, 43.16, 21.97, 21.81, 10.48 ppm; HRMS(EI) for C$_{17}$H$_{24}$N$_1$O$_6$[M+H]$^+$ Calcd: 338.15981 Found: 338.16336; HPLC [Chiralcel AD-H, hexane/2-propanol=95/5, 1.0 mL/min, λ=254 nm, retention times: (major) 18.4 min, (minor) 38.9 min].

(2g) 77% yield; $[\alpha]_D^{20}$=−3.56 (c 2.33, CH$_2$Cl$_2$); $^1$H NMR (300 MHz, CDCl$_3$) δ 7.44~7.42 (d, J=8.5 Hz, 2H), 7.13~7.11 (d, J=8.2 Hz, 2H), 4.88~4.81 (m, 2H), 4.22~4.16 (m, 3H), 4.04~3.97 (q, J=7.1, 6.9 Hz, 2H), 3.78~3.75 (d, J=9.4 Hz, 1H), 1.26~1.21 (t, J=7.2, 7.1 Hz, 3H), 1.08~1.03 (t, J=7.1, 7.1 Hz, 3H) ppm; $^{13}$C NMR (100 MHz, CDCl$_3$) δ 167.42, 166.83, 135.52, 132.29, 130.00, 122.62, 77.55, 62.50, 62.26, 54.86, 42.60, 14.17, 13.99 ppm; IR (KBr) 2983, 2950, 1732, 1556, 1490, 1445 cm$^{-1}$ HRMS(ESI) for C$_{15}$H$_{19}$N$_1$O$_6$Br[M+H]$^+$ Calcd: 388.03903 Found: 388.04495; HPLC [Chiralcel AD-H, hexane/ethanol=95/5, 1.0 mL/min, λ=254 nm, retention times: (major) 35.9 min, (minor) 44.4 min].

(2h) $[\alpha]_D^{20}$=−0.24 (c 0.43, CH$_2$Cl$_2$); $^1$H NMR (300 MHz, CDCl$_3$) δ 7.29~7.17 (dd, J=20.6, 8.2 Hz, 4H), 4.88~4.81 (m, 2H), 4.23~4.16 (m, 3H), 4.04~3.97 (q, J=7.1, 7.1 Hz, 2H), 3.78~3.75 (d, J=9.3 Hz, 1H), 1.26~1.21 (t, J=7.1, 7.2 Hz, 3H), 1.08~1.03 (t, J=7.2, 6.8 Hz, 3H) ppm; $^{13}$C NMR (100 MHz, CDCl$_3$) δ 167.44, 166.83, 134.98, 134.46, 129.69, 129.32, 77.63, 62.49, 62.23, 54.92, 42.55, 14.15, 13.97 ppm; IR (KBr) 2984, 1733, 1557, 1478, 1445, 1371 cm-1 HRMS (ESI) for C$_{15}$H$_9$N$_1$O$_6$Cl[M+H]$^+$ Calcd: 344.08954 Found: 344.09119; HPLC [Chiralcel AD-H, hexane/ethanol=90/10, 1.0 mL/min, λ=254 nm, retention times: (major) 17.9 min, (minor) 24.1 min].

(2i) 60% yield; $[\alpha]_D^{20}$=−1.56 (c 1.33, CH$_2$Cl$_2$); $^1$H NMR (300 MHz, CDCl$_3$) δ 7.09 (d, J=15.2 Hz, 4H), 4.89~4.78 (m, 2H), 4.22~4.14 (m, 3H), 4.01~3.96 (q, J=7.0, 7.1 Hz, 2H), 3.79 (d, J=9.3 Hz, 1H), 2.27 (s, 3H), 1.25~1.22 (t, J=7.1, 7.0 Hz, 3H), 1.06~1.02 (t, J=7.1, 8.6 Hz, 3H) ppm; $^{13}$C NMR (100 MHz, CDCl$_3$) δ 167.74, 167.08, 138.27, 138.23, 133.30, 129.80, 128.05, 78.00, 62.32, 62.06, 55.24, 42.84, 21.28, 14.18, 13.97 ppm; IR(KBr) 3030, 2987, 1732, 1612, 1557 cm$^{-1}$; HRMS(ESI) for C$_{16}$H$_{22}$N$_1$O$_6$ [M+H]$^+$ Calcd: 324.14416 Found: 324.14648; HPLC [Chiralcel AD-H, hexane/ethanol=98/2, 1.0 mL/min, λ=254 nm, retention times: (major) 36.0 min, (minor) 42.8 min].

(2j) 40% yield; $[\alpha]_D^{20}$=−1.56 (c=0.50, CH$_2$Cl$_2$); $^1$H NMR (300 MHz, CDCl$_3$) δ 7.09~7.06 (d, J=8.3 Hz, 2H), 6.72~6.70 (d, J=8.2 Hz, 2H), 5.63 (br, 1H), 4.91~4.74 (m, 2H), 4.25~4.12 (m, 3H), 4.05~3.98 (q, J=7.1, 6.8 Hz, 2H), 3.79 (d, J=9.7 Hz, 1H), 1.29~1.24 (t, J=7.1, 6.6 Hz, 3H), 1.09~1.05 (t, J=7.1, 7.2 Hz, 3H) ppm; $^{13}$C NMR (100 MHz, CDCl$_3$) δ 167.74, 167.28, 155.88, 129.54, 128.06, 78.17, 62.44, 62.23, 55.29, 42.53, 29.92, 14.20, 14.00 ppm; HRMS (ESI) for C$_{15}$H$_{20}$N$_1$O$_7$[M+H]$^+$ Calcd: 326.12343 Found: 326.12903; HPLC [Chiralcel AD-H, hexane/ethanol=90/10, 1.0 mL/min, λ=254 nm, retention times: (major) 20.4 min, (minor) 50.6 min].

(2k) 47% yield; $[\alpha]_D^{20}$=−1.37 (c 0.80, CH$_2$Cl$_2$); $^1$H NMR (300 MHz, CDCl$_3$) δ 7.16~7.13 (d, J=8.5 Hz, 2H), 6.84~6.81 (d, J=8.8 Hz, 2H), 4.87~4.80 (m, 2H), 4.24~4.16

(m, 3H), 4.04~3.97 (q, J=7.1, 7.1 Hz, 2H), 3.79~3.78 (d, J=2.7 Hz, 1H), 3.76 (s, 3H), 1.28~1.23 (t, J=7.1, 7.2 Hz, 3H), 1.08~1.03 (t, J=7.1, 7.1 Hz, 3H) ppm; $^{13}$C NMR (100 MHz, CDCl$_3$) δ 167.73, 167.08, 159.61, 129.36, 128.17, 114.48, 78.12, 62.34, 62.06, 55.42, 55.30, 42.53, 14.19, 14.01 ppm; IR(KBr) 2988, 2936, 2904, 1730, 1612, 1552 cm-1 HRMS (ESI) for C$_{16}$H$_{22}$N$_1$O$_7$[M+H]$^+$ Calcd: 340.13908 Found: 340.13901; HPLC [Chiralcel AD-H, hexane/ethanol=90/10, 1.0 mL/min, λ=254 nm, retention times: (major) 23.8 min, (minor) 39.5 min].

(2l) 51% yield; $[α]_D^{20}$=-7.08 (c 1.30, CH$_2$Cl$_2$); $^1$H NMR (300 MHz, CDCl$_3$) δ 7.26~7.21 (m, 1H), 7.15~7.12 (m, 1H), 6.87~6.83 (m, 2H), 5.06~4.98 (dd, J=3.6, 1.1 Hz, 1H), 4.89~4.83 (dd, J=3.6, 1.1 Hz, 1H), 4.37~4.34 (m, 1H), 4.24~4.12 (m, 3H), 3.97~3.90 (q, J=7.2, 7.2 Hz, 2H), 3.85 (s, 3H), 1.28~1.23 (t, J=7.1, 6.9 Hz, 3H), 1.01~0.96 (t, J=7.2, 7.1 Hz, 3H) ppm; $^{13}$C NMR (100 MHz, CDCl$_3$) δ 168.14, 167.41, 157.62, 131.09, 129.83, 123.87, 120.96, 111.27, 76.40, 62.18, 61.77, 55.62, 52.89, 40.74, 14.20, 13.94 ppm; IR (KBr) 2984, 2939, 2908, 1732, 1613, 1556 cm-1 HRMS (ESI) for C$_{16}$H$_{22}$N$_1$O$_6$ [M] Calcd: 339.13125 Found: 339.12933; HPLC [Chiralcel AD-H, hexane/2-propanol=95/5, 1.0 mL/min, λ=254 nm, retention times: (major) 14.9 min, (minor) 20.6 min].

(2m) 78% yield; $[α]_D^{20}$=+5.06 (c 0.33, CH$_2$Cl$_2$); $^1$H NMR (300 MHz, CDCl$_3$) δ 7.34~7.26 (d, J=23.9 Hz, 1H), 6.29~6.28 (t, J=2.9, 1.6 Hz, 1H), 6.22~6.21 (d, J=3.0 Hz, 1H), 4.91~4.88 (m, 2H), 4.39~4.37 (m, 1H), 4.25~4.11 (m, 4H), 3.91~3.88 (d, J=7.9 Hz, 1H), 1.28~1.23 (t, J=7.1, 6.9 Hz, 3H), 1.22~1.17 (t, J=7.1, 6.9 Hz, 3H) ppm; $^{13}$C NMR (100 MHz, CDCl$_3$) δ 167.35, 167.04, 149.74, 142.95, 110.74, 108.67, 75.64, 62.38, 53.20, 37.03, 29.92, 14.17, 14.11 ppm; IR (KBr) 2985, 2940, 1734, 1559, 1506, 1466, 1448; HRMS(ESI) for C$_{13}$H$_{18}$N$_1$O$_7$[M+H]$^+$ Calcd: 300.10778 Found: 300.10742; HPLC [Chiralcel AD-H, hexane/2-propanol=95/5, 0.6 mL/min, λ=254 nm, retention times: (major) 22.7 min, (minor) 29.2 min].

(2n) $[α]_D^{20}$=-24.29 (c 0.03, CH$_2$Cl$_2$); $^1$H NMR (400 MHz, CDCl$_3$) δ 7.99 (s, 1H), 7.27 (d, J=8.2 Hz, 2H), 7.17~7.14 (d, J=8.2 Hz, 2H), 4.20~4.13 (q, J=6.9, 6.9 Hz, 1H), 4.06~3.97 (q, J=6.9 Hz, 1H), 3.77~3.71 (m, 1H), 3.50~3.46 (d, J=10.1 Hz, 1H), 3.37~3.31 (t, J=9.4, 9.4 Hz, 1H), 1.23~1.18 (t, J=7.1 Hz, 3H) ppm; HRMS(EI) for C$_{13}$H$_{15}$NO$_3$[M+H]$^+$ Calcd: 233.1052, Found: 233.1051.

(2o) $[α]_D^{20}$=-24.29 (c 0.03, CH$_2$Cl$_2$); $^1$H NMR (300 MHz, CDCl$_3$) δ 7.99 (s, 1H), 7.27 (d, J=8.2 Hz, 2H), 7.17~7.14 (d, J=8.2 Hz, 2H), 4.20~4.13 (q, J=6.9, 6.9 Hz, 1H), 4.06~3.97 (q, J=6.9 Hz, 1H), 3.77~3.71 (m, 1H), 3.50~3.46 (d, J=10.1 Hz, 1H), 3.37~3.31 (t, J=9.4, 9.4 Hz, 1H), 1.23~1.18 (t, J=7.1 Hz, 3H) ppm; $^{13}$C NMR (100 MHz, CDCl$_3$) δ 173.15, 169.30, 138.47, 133.51, 129.31, 128.67, 62.11, 55.65, 47.92, 44.04, 14.35 ppm; IR (KBr) 3435, 3229, 3017, 2360, 1710, 1493 cm$^{-1}$; HRMS(ESI) for C$_{13}$H$_{14}$C$_1$N$_{03}$[M+H]$^+$ Calcd: 267.06567, Found: 267.1026.

(2p) $[α]_D^{20}$=+3.12 (c 2.33, MeOH); $^1$H NMR (400 MHz, D$_2$θ) δ 7.27~7.19 (m, 5H), 3.21 (m, 2H), 3.11~3.08 (d, 1H), 2.69 (dd, 1H, J=16.0, 6.0 Hz), 2.59~2.55 (dd, J=16.5, 8.5 Hz) ppm; $^{13}$C NMR (100 MHz, DMSO-d$_6$) δ 175.29, 138.61, 129.57, 128.11, 44.10, 39.94, 38.35 ppm; HRMS (EI$^+$) for C$_9$H$_{12}$C$_1$NO$_2$[M+HCl]$^+$ Calcd: 201.0557, Found: 201.0563.

(2q) $[α]_D^{20}$=-3.79 (c 2.33, H$_2$O); $^1$H NMR (300 MHz, DMSO-d$_6$) δ 8.25 (s, 3H), 7.35 (m, 4H), 3.08 (m, 1H), 2.92 (m, 2H), 2.57 (dd, J=9.5, 16.5 Hz) ppm; 13C NMR (100 MHz, DMSO-d$_6$) δ 173.17, 141.20, 132.50, 130.69, 129.36, 129.28, 128.59, 127.93, 44.15, 39.1, 38.66 ppm; HRMS (FAB$^+$) for C$_{10}$H$_{12}$C$_1$NO$_2$[M+H]$^+$ Calcd: 214.0635, Found: 214.0637.

(3a) $[α]_D^{20}$=-18.5 (c 1.0, CHCl$_3$); $^1$H NMR (500 MHz, CDCl$_3$) δ 7.91~7.92 (m, 2H), 7.59~7.26 (m, 8H), 4.85~4.81 (dd, J=12.5, 6.7 Hz, 1H), 4.71~4.67 (dd, J=12.5, 7.8 Hz, 1H), 4.26~4.20 (m, 1H), 3.51~3.46 (dd, J=17.7, 6.4 Hz, 1H), 3.45~3.40 (dd, J=17.7, 7.5 Hz, 1H) ppm; $^{13}$C NMR (125 MHz, CDCl$_3$) δ 196.87, 139.15, 136.39, 133.60, 129.09, 128.77, 128.04, 127.90, 127.48, 79.58, 41.54, 39.30 ppm; IR (KBr) 3058, 3029, 2920, 1687, 1544, 1440, 1367, 1268, 1224, 1084, 988, 764, 703, 623, 559 cm$^{-1}$; LRMS (ESI$^+$) for C$_{16}$H$_{15}$NO$_3$ [M+Na]$^+$ Calcd: 292.1, Found: 292.1; HPLC [Chiralcel AD-H, hexane/2-propanol=90/10, flow rate=1.0 mL/min, λ=254 nm, retention times: (major) 12.8 min, (minor) 17.4 min]; R$_f$ (SiO$_2$, EtOAc/n-hexane=1/5)=0.40

(3b) $[α]_D^{20}$=-24.7 (c 1.0, CH$_2$Cl$_2$); $^1$H NMR (500 MHz, CDCl$_3$) δ 7.92~7.90 (m, 2H), 7.60~7.57 (m, 1H), 7.48~7.45 (m, 2H), 7.32~7.29 (m, 2H), 7.24~7.22 (m, 2H), 4.83~4.80 (dd, J=12.5, 6.5 Hz, 1H), 4.68~4.64 (dd, J=12.5, 8.1 Hz, 1H), 4.25~4.19 (m, 1H), 3.48~3.43 (dd, J=18.2, 6.4 Hz, 1H), 3.43~3.38 (dd, J=18.2, 7.3 Hz, 1H) ppm; $^{13}$C NMR (125 MHz, CDCl$_3$) δ 196.50, 137.59, 136.23, 133.74, 129.27, 128.90, 128.82, 128.02, 79.36, 41.36, 38.70 ppm; LRMS (ESI$^+$) for C$_{16}$H$_{14}$C$_1$NO$_3$ [M+Na]$^+$ Calcd: 326.1, Found: 326.1; HPLC [Chiralcel AD-H, hexane/2-propanol=95/5, flow rate=1.0 mL/min, λ=254 nm, retention times: (major) 24.3 min, (minor) 37.5 min]; R$_f$(SiO$_2$, EtOAc/n-hexane=1/5)=0.31

(3c) $[α]_D^{20}$=-19.4 (c 1.0, CHCl$_3$); $^1$H NMR (500 MHz, CDCl$_3$) δ 7.91 (d, J=7.0 Hz, 2H), 7.57 (t, J=7.5 Hz, 1H), 7.45 (t, J=8.0 Hz, 2H), 7.18~7.13 (m, 4H), 4.83~4.79 (dd, J=12.5, 6.5 Hz, 1H), 4.68~4.64 (dd, J=12.5, 8.0 Hz, 1H), 4.22~4.16 (m, 1H), 3.48~3.44 (dd, J=17.5, 6.5 Hz, 1H), 3.43~3.38 (dd, J=18.0, 7.5 Hz, 1H), 2.31 (s, 3H) ppm; $^{13}$C NMR (125 MHz, CDCl$_3$) δ 196.96, 137.60, 136.42, 136.05, 133.56, 129.76, 128.75, 128.05, 127.31, 79.73, 41.59, 38.96, 21.07 ppm; IR (KBr) 3058, 2922, 2862, 1685, 1551, 1516, 1446, 1377, 1270, 1225, 998, 817, 755, 691, 551 cm$^{-1}$; LRMS (ESI$^+$) for C$_{17}$H$_{17}$NO$_3$ [M+Na]$^+$ Calcd: 306.1, Found: 306.2; HPLC [Chiralcel AD-H, hexane/2-propanol=90/10, flow rate=1.0 mL/min, λ=254 nm, retention times: (major) 11.9 min, (minor) 16.3 min]; R$_f$ (SiO$_2$, EtOAc/n-hexane=1/10)=0.33

(3d) $[α]_D^{20}$=-25.8 (c 1.0, CHCl$_3$); $^1$H NMR (500 MHz, CDCl$_3$) δ 7.90 (d, J=7.0 Hz, 2H), 7.58 (t, J=7.5 Hz, 1H), 7.48~7.45 (m, 4H), 7.18~7.16 (m, 2H), 4.83~4.79 (dd, J=12.5, 6.5 Hz, 1H), 4.68~4.64 (dd, J=12.5, 8.5 Hz, 1H), 4.23~4.17 (m, 1H), 3.48~3.43 (dd, J=17.0, 6.5 Hz, 1H), 3.43~3.38 (dd, J=17.0, 7.0 Hz, 1H) ppm; 13C NMR (125 MHz, CDCl$_3$) δ 196.47, 138.14, 136.21, 133.74, 132.22, 129.24, 128.82, 128.02, 121.85, 79.28, 41.30, 38.76 ppm; LRMS (ESI$^+$) for C$_{16}$H$_{14}$BrNO$_3$ [M+Na]$^+$ Calcd: 370.0, Found: 370.1; HPLC [Chiralcel AD-H, hexane/2-propanol=90/10, flow rate=1.0 mL/min, λ=254 nm, retention times: (major) 16.4 min, (minor) 22.4 min]; R$_f$(SiO$_2$, EtOAc/n-hexane=1/5)=0.30

(3e) $[α]_D^{20}$=-24.7 (c 1.0, CH$_2$Cl$_2$); $^1$H NMR (500 MHz, CDCl$_3$) δ 7.92~7.90 (m, 2H), 7.60~7.57 (m, 1H), 7.48~7.45 (m, 2H), 7.32~7.29 (m, 2H), 7.24~7.22 (m, 2H), 4.83~4.80 (dd, J=12.5, 6.5 Hz, 1H), 4.68~4.64 (dd, J=12.5, 8.1 Hz, 1H), 4.25~4.19 (m, 1H), 3.48~3.43 (dd, J=18.2, 6.4 Hz, 1H), 3.43~3.38 (dd, J=18.2, 7.3 Hz, 1H) ppm; $^{13}$C NMR (125 MHz, CDCl$_3$) δ 196.50, 137.59, 136.23, 133.74, 129.27, 128.90, 128.82, 128.02, 79.36, 41.36, 38.70 ppm; LRMS (ESI$^+$) for C$_{16}$H$_{14}$C$_1$NO$_3$ [M+Na]$^+$ Calcd: 326.1, Found: 326.1; HPLC [Chiralcel AD-H, hexane/2-propanol=95/5, flow rate=1.0 mL/min, λ=254 nm, retention times: (major) 24.3 min, (minor) 37.5 min]; $R_f$(SiO$_2$, EtOAc/n-hexane=1/5)=0.31

(3f) $[\alpha]_D^{20}$ –20.2 (c 1.0, CHCl$_3$); $^1$H NMR (500 MHz, CDCl$_3$) δ 7.93~7.91 (m, 2H), 7.59~7.44 (m, 3H), 7.20 (d, J=8.7 Hz, 2H), 6.86 (d, J=8.7, 2H), 4.82~4.78 (dd, J=12.3, 6.7 Hz, 1H), 4.67~4.63 (dd, J=12.3, 7.9 Hz, 1H), 4.21~4.15 (m, 1H), 3.78 (s, 3H), 3.47~3.43 (dd, J=16.5, 6.5 Hz, 1H), 3.43~3.37 (dd, J=16.5, 6.6 Hz, 1H) ppm; $^{13}$C NMR (125 MHz, CDCl$_3$) δ 196.99, 159.10, 136.42, 133.56, 130.99, 128.75, 128.52, 128.04, 114.45, 79.85, 55.27, 41.67, 38.65 ppm; LRMS (ESI$^+$) for C$_{17}$H$_{17}$NO$_4$ [M+Na]$^+$ Calcd: 322.1, Found: 322.2; HPLC [Chiralcel AD-H, hexane/2-propanol=80/20, flow rate=1.0 mL/min, λ=254 nm, retention times: (major) 11.8 min, (minor) 16.0 min]; $R_f$(SiO$_2$, EtOAc/n-hexane=1/5)=0.31

(3g) $[\alpha]_D^{20}$ –5.2 (c 1.4, CHCl$_3$); $^1$H NMR (500 MHz, CDCl$_3$) δ 7.94~7.92 (m, 2H), 7.58~7.55 (m, 1H), 7.47~7.44 (m, 2H), 7.26~7.20 (m, 2H), 6.92~6.88 (m, 2H), 4.89~4.82 (m, 2H), 4.45~4.39 (m, 1H), 3.86 (s, 3H), 3.54 (d, J=7.5 Hz, 2H) ppm; 13C NMR (125 MHz, CDCl$_3$) δ 197.64, 157.20, 136.63, 133.38, 129.52, 128.99, 128.68, 128.05, 126.70, 120.96, 110.05, 77.90, 55.38, 39.80, 35.95 ppm; IR (KBr) 3063, 2923, 2852, 1684, 1598, 1550, 1494, 1445, 1377, 1246, 1120, 1025, 754, 690 cm$^{-1}$; LRMS (ESI$^+$) for C$_{17}$H$_{17}$NO$_4$ [M+Na]$^+$ Calcd: 322.1, Found: 322.2; HPLC [Chiralcel AD-H, hexane/2-propanol=85/15, flow rate=1.0 mL/min, λ=254 nm, retention times: (major) 9.4 min, (minor) 12.7 min]; $R_f$(SiO$_2$, EtOAc/n-hexane=1/5)=0.30

(3h) $[\alpha]_D^{20}$ –12.9 (c 1.0, CHCl$_3$); $^1$H NMR (500 MHz, CDCl$_3$) δ 7.96~7.94 (m, 2H), 7.61~7.58 (m, 1H), 7.49~7.46 (m, 2H), 7.34 (m, 1H), 6.30~6.29 (m, 1H), 6.19 (d, J=3.3 Hz, 1H), 4.83~4.79 (dd, J=11.6, 5.4 Hz, 1H), 4.77~4.73 (dd, J=11.6, 6.0 Hz, 1H), 4.36~4.31 (m, 1H), 3.55~3.50 (dd, J=17.7, 6.1 Hz, 1H), 3.46~3.41 (dd, J=17.7, 7.3 Hz, 1H) ppm; $^{13}$C NMR (125 MHz, CDCl$_3$) δ 196.55, 151.95, 142.32, 136.26, 133.69, 128.80, 128.07, 110.53, 107.20, 77.27, 38.99, 33.19 ppm; IR (KBr) 3121, 3062, 2918, 1685, 1596, 1553, 1505, 1448, 1377, 1213, 1183, 1012, 917, 749, 691, 599 cm$^{-1}$; LRMS(ESI$^+$) for C$_{14}$H$_{13}$NO$_4$ [M+Na]$^+$ Calcd: 282.1, Found: 282.1; HPLC [Chiralcel AD-H, hexane/2-propanol=95/5, flow rate=1.0 mL/min, λ=254 nm, retention times: (major) 12.9 min, (minor) 15.6 min]; $R_f$ (SiO$_2$, EtOAc/n-hexane=1/5)=0.32

(3i) $^1$H NMR (500 MHz, CDCl$_3$) δ 7.38~7.16 (m, 8H), 6.87~6.85 (m, 2H), 4.75~4.71 (dd, J=11.6, 6.6 Hz, 1H), 4.68~4.64 (dd, J=11.6, 6.4 Hz, 1H), 4.10~4.04 (m, 1H), 3.04~3.0 (dd, J=13.7, 4.6 Hz, 1H), 2.99~2.94 (dd, J=13.7, 5.6 Hz, 1H) ppm; $^{13}$C NMR (125 MHz, CDCl$_3$) δ 169.33, 150.33, 137.96, 129.50, 129.22, 128.29, 127.55, 126.12, 121.39, 79.38, 40.38, 37.87 ppm; LRMS (ESI$^+$) for C$_{16}$H$_{15}$NO$_4$ [M+Na]$^+$ Calcd: 308.1, Found: 308.1; $R_f$(SiO$_2$, EtOAc/n-hexane=1/5)=0.40.

(3j) $^1$H NMR (500 MHz, CDCl$_3$) δ 7.35~7.22 (m, 7H), 6.92~6.90 (m, 2H), 4.79~4.75 (dd, J=12.7, 7.3 Hz, 1H), 4.71~4.67 (dd, J=12.7, 7.9 Hz, 1H), 4.11~4.06 (m, 1H), 3.08~3.03 (dd, J=14.7, 5.3 Hz, 1H), 3.01~2.96 (dd, J=14.7, 6.5 Hz, 1H) ppm; $^{13}$C NMR (125 MHz, CDCl$_3$) δ 169.01, 150.17, 136.37, 134.23, 129.53, 129.43, 128.88, 126.20, 121.26, 79.08, 39.70, 37.67 ppm; LRMS (ESI$^+$) for C$_{16}$H$_{14}$C$_1$NO$_4$ [M+Na]$^+$ Calcd: 342.1, Found: 342.1; $R_f$(SiO$_2$, EtOAc/n-hexane=1/5)=0.31.

(3k) $[\alpha]_D^{20}$=+36.0 (c 0.01, CHCl$_3$)

(3l) $[\alpha]_D^{20}$=–36.4 (c 0.01, CHCl$_3$); $^1$H NMR (500 MHz, CDCl$_3$) δ 7.37~7.33 (m, 2H), 7.29~7.27 (m, 2H), 7.26~7.25 (m, 1H), 5.92 (br s, 1H), 3.81~3.77 (m, 1H), 3.71 (q, J=8.0 Hz, 1H), 3.45~3.41 (dd, J=9.4, 2.0 Hz, 1H), 2.77~2.72 (dd, J=16.8, 8.7 Hz, 1H), 2.54~2.49 (dd, J=17.0, 8.5 Hz, 1H) ppm; $^{13}$C NMR (125 MHz, CDCl$_3$) δ 177.93, 142.14, 128.88, 127.13, 126.79, 49.60, 40.31, 38.02 ppm; LRMS (ESI$^+$) for C$_{10}$H$_{11}$NO[M+H]$^+$ Calcd: 162.10, Found: 162.20.

(3m) $[\alpha]_D^{22}$=+33.0 (c 1.0, EtOH)

(3n) $[\alpha]_D^{30}$=–39.7 (c 1.00, CHCl$_3$); $^1$H NMR (500 MHz, CDCl$_3$) δ 7.32 (d, J=8.5 Hz, 2H), 7.19 (d, J=8.3 Hz, 2H), 5.72 (br s, 1H), 3.80~3.77 (m, 1H), 3.69 (q, J=8.5 Hz, 1H), 3.40~3.36 (dd, J=8.4, 2.5 Hz, 1H), 2.77~2.71 (dd, J=17.8, 8.5 Hz, 1H), 2.48~2.43 (dd, J=16.9, 8.5 Hz, 1H) ppm; $^{13}$C NMR (125 MHz, CDCl$_3$) δ 177.68, 140.59, 132.93, 129.03, 128.15, 49.49, 39.66, 37.90 ppm; HRMS (ESI$^+$) for C$_{10}$H$_{10}$ClNO [M+H]$^+$ Calcd: 196.0445, Found: 196.1160.

(3o) $[\alpha]_D^{25}$=+5.8 (c 0.5, H$_2$O); $^1$H NMR (500 MHz, D$_2$O) δ 7.47~7.44 (m, 2H), 7.41~7.36 (m, 3H), 3.47~3.36 (m, 2H), 3.27 (t, J=11.0 Hz, 1H), 2.89~2.85 (dd, J=16.0, 5.9 Hz, 1H), 2.81~2.76 (dd, J=16.0, 8.8 Hz, 1H) ppm; $^{13}$C NMR (125 MHz, D$_2$O) δ 175.62, 138.37, 129.37, 128.30, 127.87, 43.81, 40.0, 38.34 ppm; LRMS (ESI$^+$) for C$_{10}$H$_{13}$NO$_2$[M+H]$^+$ Calcd: 180.1, Found: 180.2; $R_f$(SiO$_2$, CH$_2$Cl$_2$/MeOH=10/1) =0.48.

(3p) $[\alpha]_D^{25}$=+1.8 (c 0.5, H$_2$O); $^1$H NMR (500 MHz, D$_2$O) δ 7.40~7.37 (m, 2H), 7.29~7.26 (m, 2H), 3.39~3.30 (m, 2H), 3.22~3.16 (m, 1H), 2.81~2.76 (dd, J=16.1, 5.9 Hz, 1H), 2.70~2.65 (dd, J=16.1, 8.9 Hz, 1H) ppm; $^{13}$C NMR (125 MHz, D$_2$O) δ 175.46, 137.02, 133.38, 129.41, 129.25, 43.60, 39.47, 38.33 ppm; HRMS (FAB$^+$) for C$_{10}$H$_{12}$C$_1$NO$_2$ [M+H]$^+$ Calcd: 214.0635, Found: 214.0627; $R_f$ (SiO$_2$, CH$_2$Cl$_2$/MeOH=10/1)=0.46.

(3q) $[\alpha]_D^{20}$=–8.4 (c=3.0, MeOH)

(3r) $[\alpha]_D^{20}$=+8.5 (c=3.0, MeOH); $^1$H NMR spectrum (CDCl$_3$), δ, ppm: 2.59 d.d (1H, 3-H, 3JHH=8.4, 2JHH=17.0 Hz), 2.81 d.d (1H, 3-H, 3JHH=8.4, 2JHH=17.0 Hz), 3.53 m (1H, 5-H), 3.63 m (1H, 4-H), 3.85 m (1H, 5-H), 3.97 d.d (2H, NCH2CO, 3JHH=16.3, 2JHH=33.0 Hz); 6.24 br.s and 6.66 br.s (1H each, NH2), 7.22~7.31 m (5H, Ph). $^{13}$C NMR spectrum (CDCl$_3$), δ, ppm: 37.48, 38.54, 46.25, 55.55, 126.89, 127.27, 129.01, 141.97, 170.78, 175.03 pp; HRMS (ESI$^+$) for C$_{10}$H$_{13}$NO$_2$ [M+Na]$^+$ Calcd: 241.0957, Found: 241.0947.

(3s) $[\alpha]_D^{25}$=–62.0 (c 1.0, MeOH); $^1$H NMR (CDCl$_3$, 500 MHz) 6.51 (s, 1H) 5.93 (s, 1H) 4.46 (dd, J=8.9, 7.9, 1H) 3.47 (dd, J=9.8, 7.8 Hz, 1H) 3.05 (dd, J=9.8, 7.1 Hz, 1H) 2.54 (dd, J=16.7, 8.6, 1H) 2.39~2.23 (m, 1H) 2.06 (dd, J=16.7, 8.1, 1H) 1.99~1.85 (m, 1H) 1.70~1.62 (m, 1H) 1.45~1.37 (m, 2H) 1.37~1.25 (m, 2H) 0.94~0.84 (m, 6H) ppm; $^{13}$C NMR (CDCl$_3$, 100 MHz) 175.4, 172.6, 55.7, 49.4, 37.8, 36.4, 31.9, 21.2, 20.5, 13.9, 10.4 ppm; HRMS calculated for [M+Na]$^+$ C$_{11}$H$_{20}$O$_2$N$_2$ 235.1422, found 235.1418.

Example 3: Reaction Test Results when Different Chiral Organocatalysts and Different Solvents were Used The Michael addition reaction described in Example 2 was carried out using each of the chiral organocatalysts prepared in Example 1 in water or toluene as the solvent (FIG. 6 and Tables 3 and 4). The reaction times and yields were investigated.

TABLE 3

| Chiral organocatalyst | R$_1$ | R$_2$ | Solvent | Time (h) | Yield (%)[b] | ee (%)[c] |
|---|---|---|---|---|---|---|
| 1d | Me | H | Water[a] | 14 | 97 | 99 |
| 1d | Me | H | Toluene | 96 | 89 | 80 |

TABLE 3-continued

| Chiral organocatalyst | $R_1$ | $R_2$ | Solvent | Time (h) | Yield (%)[b] | ee (%)[e] |
|---|---|---|---|---|---|---|
| 1j | Me | H | Water | 10 | 98 | 99 |
| 1k | Me | H | Water | 19 | 95 | 94 |
| 1j | Et | H | Water | 12 | 97 | 99 |
| 1j | Et | H | Toluene | 96 | 81 | 80 |
| 1l | Et | H | Water | 12 | 81 | 94 |
| 1l | Et | H | Toluene | 96 | 86 | 93 |
| 1j | Bn | H | Water | 14 | 93 | 98 |
| 1k | Bn | H | Water | 26 | 91 | 98 |

[a]5 equiv.,
[b]Isolated yield,
[e]ee values were decided by chiral phase HPLC using an AD-H or OD-H column)

TABLE 4

| Chiral organocatalyst | $R_1$ | $R_2$ | Solvent | Time (min) | Yield (%)[b] | ee (%)[e] |
|---|---|---|---|---|---|---|
| 1m | Et | H | — | 60 | 97 | 91 |
| 1n | Et | H | — | 60 | 95 | 99 |
| 1m | Et | H | Water | 5 | 99 | 99 |
| 1m | Et | Et | Water | 30 | 95 | 99 |
| 1n | Et | H | Water | 60 | 96 | 90 |
| 1m | Bn | H | Water | 15 | 94 | 99 |
| 1n | Bn | H | Water | 60 | 92 | 99 |
| 1m | Et | Br | Water | 10 | 95 | 99 |
| 1n | Et | Br | Water | 90 | 96 | 99 |

[a]5 equiv.,
[b]Isolated yield,
[e]ee values were decided by chiral phase HPLC using an AD-H or OD-H column)

These results reveal that the trifluoromethyl-substituted chiral organocatalysts can be used in water, indicating that the interaction between the fluorine atoms in water reduces the activation barrier.

Example 4: Reaction Test Results when Different α,β-Unsaturated Nitro Compounds were Used The Michael addition reaction described in Example 2 was carried out with each of the α,β-unsaturated nitro compounds shown in Table 5 using the chiral organocatalyst 1m prepared in Example 1 in water as the solvent. The reaction times and yields were investigated. Specifically, trans-β-nitrostyrene (1.0 equiv.), malononitrile (2.0 equiv.), and 0.1~0.001 mol % of the chiral organocatalyst 1m were added to water (0.4 ml). The mixture was stirred at room temperature (rt). The reaction conversion was monitored by TLC. After completion of the reaction, ethyl acetate (0.2 ml) was added to the reaction mixture. This solution was washed twice with water (2×1.0 mL), dried over magnesium sulfate, and concentrated to afford the desired product. The product was purified by chromatography on a silica-gel column (hexane/methylene chloride, 2:1) (FIG. 7 and Table 5).

TABLE 5

| | $R_1$ | $R_2$ | Ar | Time (h) | Yield (%)[b] | ee (%)[c] |
|---|---|---|---|---|---|---|
| 1 | Me | Me | Ph | 24 | 98 | 99 |
| 2 | Et | Et | Ph | 24 | 98 | 99 |
| 3[d] | Et | Et | Ph | 0.5 | 98 | 99 |
| 4[e] | Et | Et | Ph | 6 | 98 | 99 |
| 5 | i-Pr | i-Pr | Ph | 24 | 96 | 99 |
| 6 | n-Pr | n-Pr | Ph | 24 | 96 | 99 |
| 7 | Bu | Bu | Ph | 24 | 99 | 99 |
| 8 | Et | Et | 4-Br—Ph | 24 | 94 | 99 |
| 9 | Et | Et | 4-Cl—Ph | 24 | 95 | 99 |
| 10 | Et | Et | 4-Me—Ph | 24 | 91 | 93 |

TABLE 5-continued

| | $R_1$ | $R_2$ | Ar | Time (h) | Yield (%)[b] | ee (%)[c] |
|---|---|---|---|---|---|---|
| 11 | Et | Et | 4-OMe—Ph | 24 | 93 | 91 |
| 12 | Et | Et | 2-OMe—Ph | 24 | 91 | 96 |
| 13 | Et | Et | 4-OH—Ph | 24 | 95 | 96 |
| 14 | Et | Et | furyl | 24 | 97 | 99 |

[b]Isolated yield,
[c]ee values were decided by chiral phase HPLC,
[d]reaction in 0.1 mol % catalyst,
[e]reaction in 0.01 mol % catalyst)

Example 5: Reaction Test Results when Different α,β-Unsaturated Ketone (Trans-Chalcone) Compounds were Used The Michael addition reaction described in Example 2 was carried out with each of the nitroethyl esters shown in Table 6 was carried out using the chiral organocatalyst 1m prepared in Example 1 and water as the solvent. The reaction times and yields were investigated. Specifically, an α,β-unsaturated ketone (1.0 equiv.), the nitroethyl ester (2.0 equiv.), and 0.1~0.009 mol % of the chiral organocatalyst 1m were added to water (0.4 ml). The mixture was stirred at room temperature (rt). The reaction conversion was monitored by TLC. After completion of the reaction, sodium hydroxide (1.0 equiv.) and ethanol were added to the reaction mixture, followed by stirring at room temperature for 12 h. The resulting mixture was concentrated in vacuo to afford the desired product. The product was purified by chromatography on a silica-gel column (hexane/ethyl acetate, 10:1) (FIG. 8 and Table 6).

TABLE 6

| | Ar | Time (h) | Yield (%)[b] | ee (%)[c] |
|---|---|---|---|---|
| 1 | $C_6H_5$ | 24 | 85 | 99 |
| 2 | $4\text{-MeC}_6H_4$ | 24 | 82 | 88 |
| 3 | $4\text{-BrC}_6H_4$ | 24 | 83 | 92 |
| 4 | $4\text{-ClC}_6H_4$ | 24 | 80 | 92 |
| 5 | $4\text{-MeOC}_6H_4$ | 24 | 78 | 94 |
| 6 | $2\text{-MeOC}_6H_4$ | 24 | 75 | 82 |
| 7 | 2-furyl | 24 | 83 | 98 |

[b]Isolated yield,
[c]ee values were decided by chiral phase HPLC)

General Experimental Methods

IR spectra were recorded on a NICOLET 380 FT-IR spectrophotometer. Optical rotations were performed with a Rudolph Automatic polarimeter (model name: A20766 APV/6w). $^1$H NMR spectra were recorded on a Varian Mercury 400 (400 MHz) or Varian Mercury 300 (300 MHz) with TMS as an internal reference. $^{13}$C NMR spectra were recorded on a Varian Mercury 400 (400 MHz) with TMS or $CDCl_3$ as an internal reference. Chiral HPLC analysis was performed on a Jasco LC-1500 Series HPLC system with a UV detector. All experiments were performed in oven-dried glass flasks under an argon atmosphere. Toluene ($CaH_2$) and THF (Na, benzophenone) were dried by distillation before use.

Although the particulars of the present invention have been described in detail, it will be obvious to those skilled in the art that such particulars are merely preferred embodiments and are not intended to limit the scope of the present invention. Therefore, the substantial scope of the present invention is defined by the appended claims and their equivalents.

INDUSTRIAL APPLICABILITY

The chiral bifunctional organocatalyst of the present invention is highly enantioselective and can be easily synthesized. The use of the chiral organocatalyst enables the production of γ-amino acids with high enantioselectivity in high yield in an economical and simple manner. In addition, even a small amount of the chiral organocatalyst is sufficient for mass production of various unnatural γ-amino acids with R configuration in high optical purity. Therefore, the chiral organocatalyst of the present invention can be widely utilized in various industrial fields, including the pharmaceutical industry.

The invention claimed is:

1. A chiral organocatalyst selected from the group consisting of the following compounds:

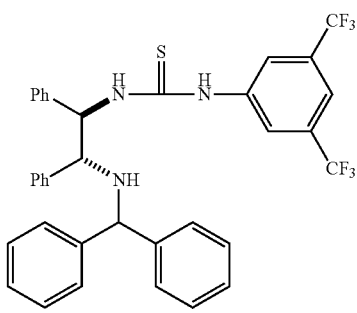

1j

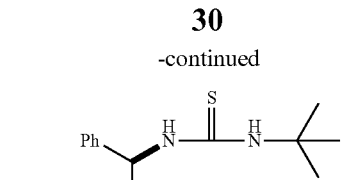

1k

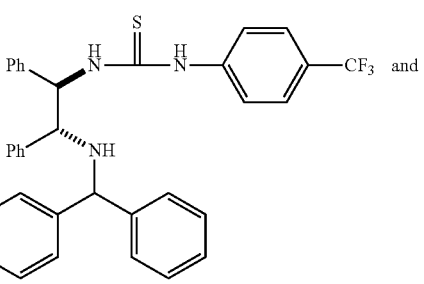

1l

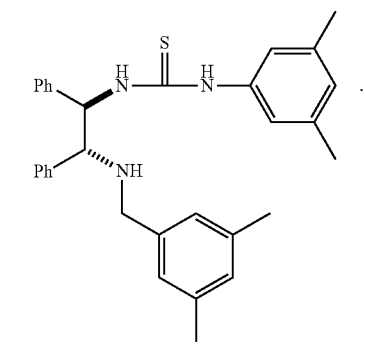

1n

* * * * *